US011173198B2

(12) United States Patent
Sun

(10) Patent No.: US 11,173,198 B2
(45) **Date of Patent: *Nov. 16, 2021**

(54) **IMMUNOGENIC PROTEINS AGAINST *CLOSTRIDIUM DIFFICILE***

(71) Applicant: UNIVERSITY OF SOUTH FLORIDA, Tampa, FL (US)

(72) Inventor: Xingmin Sun, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/786,350

(22) Filed: Feb. 10, 2020

(65) Prior Publication Data

US 2020/0230223 A1 Jul. 23, 2020

Related U.S. Application Data

(63) Continuation of application No. 15/992,497, filed on May 30, 2018, now Pat. No. 10,555,992.

(60) Provisional application No. 62/513,247, filed on May 31, 2017.

(51) Int. Cl.

| | |
|---|---|
| *A61K 39/002* | (2006.01) |
| *A61K 39/08* | (2006.01) |
| *A61P 31/04* | (2006.01) |
| *A61K 39/112* | (2006.01) |
| *A61K 38/16* | (2006.01) |
| *C07K 19/00* | (2006.01) |
| *C07K 14/255* | (2006.01) |
| *C07K 14/33* | (2006.01) |
| *A61K 39/00* | (2006.01) |

(52) U.S. Cl.
CPC ............ *A61K 39/08* (2013.01); *A61K 38/164* (2013.01); *A61K 39/0275* (2013.01); *A61P 31/04* (2018.01); *C07K 14/255* (2013.01); *C07K 14/33* (2013.01); *C07K 19/00* (2013.01); *A61K 2039/541* (2013.01); *A61K 2039/543* (2013.01); *A61K 2039/55561* (2013.01); *A61K 2039/6037* (2013.01); *A61K 2039/6068* (2013.01); *C07K 2319/03* (2013.01); *C07K 2319/55* (2013.01); *C07K 2319/74* (2013.01); *C12Y 204/00* (2013.01); *C12Y 304/00* (2013.01)

(58) Field of Classification Search
None
See application file for complete search history.

(56) References Cited

U.S. PATENT DOCUMENTS

| | | | |
|---|---|---|---|
| 2015/0044250 | A1 | 2/2015 | Heinrichs et al. |
| 2015/0132333 | A1 | 5/2015 | Scarselli et al. |
| 2016/0074496 | A1 | 3/2016 | Lanis et al. |
| 2016/0326222 | A1 | 11/2016 | Logan et al. |

OTHER PUBLICATIONS

Babcock et al., "Human monoclonal antibodies directed against toxins A and B prevent Clostridium difficile-induced mortality in hamsters," Infect Immun (2006) 74(11): pp. 6339-6347.
Ghose et al., "Toll-like receptor 5-dependent immunogenicity and protective efficacy of a recombinant fusion protein vaccine containing the nontoxic domains of Clostridium difficile toxins A and B and *Salmonella enterica* serovar typhimurium flagellin in a mouse model of Clostridium difficile disease," Infect Immun (2013) 81(6): pp. 2190-2196.
Jarchum et al., "Toll-like receptor 5 stimulation protects mice from acute Clostridium difficile colitis," Infect Immun. (2011) 79(4): pp. 1498-1503.

Tian et al., "A novel fusion protein containing the receptor binding domains of C. difficile toxin A and toxin B elicits protective immunity against lethal toxin and spore challenge in preclinical efficacy models," Vaccine (2012) 30(28): pp. 4249-4258.

Wang et al., "A chimeric toxin vaccine protects against primary and recurrent Clostridium difficile infection," Infection and immunity 80.8 (2012): pp. 2678-2688.

Wang et al., "A chimeric protein comprising the glucosyltransferase and cysteine proteinase domains of toxin B and the receptor binding domain of toxin A induces protective immunity against Clostridium difficile infection in mice and hamsters," Hum Vaccin ImmunotheR (2015) 11(9): pp. 2215-2222.

Wang et al.; "Novel Chimeric Protein Vaccines Against Clostridium difficile Infection"; Frontiers in Immunology, vol. 9; Published Oct. 22, 2018; 12 pages.

Wang et al.; Human Vaccine Immunotherapy 2015. 11(9): 2215-2222).

Baiban et al. (Jounal of Immunology, May 1, 2014, vol. 192 Suppl. 1,141.3 pp. VAC7P 958).

Jarchum et al. (infect. Immun. Apr. 2011. 79(4): 1498-1503.

*Primary Examiner* — Jennifer E Graser

(74) *Attorney, Agent, or Firm* — Meunier Carlin & Curfman LLC

(57) ABSTRACT

Described are immunogenic proteins against *Clostridium difficile*. Also described are compositions comprising the immunogenic proteins. Further described are methods of preventing or treating a *Clostridium difficile* infection in a subject in need thereof.

18 Claims, 16 Drawing Sheets

Specification includes a Sequence Listing.

FIGS. 1A-1D

ATGAGTTTAGTTAATAGAAAACAGTTAGAAAAAATGGCAAATGTAAGATTTCGTACTCAAGAAGATG
AATATGTTGCAATATTGGATGCTTTAGAAGAATATCATAATATGTCAGAGAATACTGTAGTCGAAAA
ATATTTAAAATTAAAAGATATAAATAGTTTAACAGATATTTATATAGATACATATAAAAAATCTGGT
AGAAATAAAGCCTTAAAAAAATTTAAGGAATATCTAGTTACAGAAGTATTAGAGCTAAAGAATAAT
AATTTAACTCCAGTTGAGAAAAATTTACATTTTGTTGCGATTGGAGGTCAAATAAATGACACTGCTAT
TAATTATATAAATCAATGGAAAGATGTAAATAGTGATTATAATGTTAATGTTTTTATGATAGTAATG
CATTTTTGATAAACACATTGAAAAAACTGTAGTAGAATCAGCAATAAATGATACACTTGAATCATT
TAGAGAAAACTTAAATGACCCTAGATTTGACTATAATAAATTCTTCAGAAAACGTATGGAAATAATT
TATGATAAACAGAAAAAATTTCATAAACTACTATAAAGCTCAAAGAGAAGAAAATCCTGAACTTATAA
TTGATGATATTGTAAAGACATATCTTTCAAATGAGTATTCAAAGGAGATAGATGAACTTAATACCTAT
ATTGAAGAATCCTTAAATAAAATTACACAGAATAGTGGAAATGATGTTAGAAACTTTGAAGAATTTA
AAAATGGAGAGTCATTCAACTTATATGAACAAGAGTTGGTAGAAAGGTGGAATTTAGCTGCTGCTTC
TGACATATTAAGAATATCTGCATTAAAAGAAATTGGTGGTATGTATTTAGATGTTAATATGTTACCAG
GAATACAACCAGACTTATTTGAGTCTATAGAGAAACCTAGTTCAGTAACAGTGGATTTTTGGGAAAT
GACAAAGTTAGAAGCTATAATGAAATACAAAGAATATATACCAGAATATACCTCAGAACATTTTGAC
ATGTTAGACGAAGAAGTTCAAAGTAGTTTTGAATCTGTTCTAGCTTCTAAGTCAGATAAATCAGAAA
TATTCTCATCACTTGGTGATATGGAGGCATCACCACTAGAAGTTAAAATTGCATTTAATAGTAAGGGT
ATTATAAATCAAGGGCTAATTTCTGTGAAAGACTCATATTGTAGCAATTTAATAGTAAAACAAATCG
AGAATAGATATAAAATATTGAATAATAGTTTAAATCCAGCTATTAGCGAGGATAATGATTTTAATAC
TACAACGAATACCTTTATTGATAGTATAATGGCTGAAGCTAATGCAGATAATGGTAGATTTATGATG
GAACTAGGAAAGTATTTAAGAGTTGGTTTCTTCCCAGATGTTAAAACTACTATTAACTTAAGTGGCCC
TGAAGCATATGCGGCAGCTTATCAAGATTTATTAATGTTTAAAGAAGGCAGTATGAATATCCATTTG
ATAGAAGCTGATTTAAGAAACTTTGAAATCTCTAAAACTAATATTTCTCAATCAACTGAACAAGAAA
TGGCTAGCTTATGGTCATTTGACGATGCAAGAGCTAAAGCTCAATTTGAAGAATATAAAAGGAATTA
TTTTGAAGGTTCTCTTGGTGAAGATGATAATCTTGATTTTTCTCAAAATATAGTAGTTGACAAGGAGT
ATCTTTTAGAAAAAATATCTTCATTAGCAAGAAGTTCAGAGAGAGGATATATACACTATATTGTTCA
GTTACAAGGAGATAAAATTAGTTATGAAGCAGCATGTAACTTATTTGCAAAGACTCCTTATGATAGT
GTACTGTTTCAGAAAAATATAGAAGATTCAGAAATTGCATATTATTATAATCCTGGAGATGGTGAAA
TACAAGAAATAGACAAGTATAAAATTCCAAGTATAATTTCTGATAGACCTAAGATTAAATTAACATT
TATTGGTCATGGTAAAGATGAATTTAATACTGATATATTTGCAGGTTTTGATGTAGATTCATTATCCA
CAGAAATAGAAGCAGCAATAGATTTAGCTAAAGAGGATATTTCTCCTAAGTCAATAGAAATAAATTT
ATTAGGAGCTAATATGTTTAGCTACTCTATCAACGTAGAGGAGACTTATCCTGGAAAATTATTACTTA
AAGTTAAAGATAAAATATCAGAATTAATGCCATCTATAAGTCAAGACTCTATTATAGTAAGTGCAAA
TCAATATGAAGTTAGAATAAATAGTGAAGGAAGAAGAGAATTATTGGATCATTCTGGTGAATGGATA
AATAAAGAAGAAAGTGGTGGCTCTGGTATAACTGGATTTGTGACTGTAGGCGATGATAAATACTACT
TTAATCCAATTAATGGTGGAGCTGCTTCAATTGGAGAGACAATAATTGATGACAAAAATTATTATTTC
AACCAAAGTGGAGTGTTACAAACAGGTGTATTTAGTACAGAAGATGGATTTAAATATTTTGCCCCAG
CTAATACACTTGATGAAAACCTAGAAGGAGAAGCAATTGATTTTACTGGAAAATTAATTATTGACGA
AAATATTTATTATTTTGATGATAATTATAGAGGAGCTGTAGAATGGAAAGAATTAGATGGTGAAATG
CACTATTTTAGCCCAGAAACAGGTAAAGCTTTTAAAGGTCTAAATCAAATAGGTGATTATAAATACT
ATTTCAATTCTGATGGAGTTATGCAAAAAGGATTTGTTAGTATAAATGATAATAAACACTATTTTGAT
GATTCTGGTGTTATGAAAGTAGGTTACACTGAAATAGATGGCAAGCATTTCTACTTTGCTGAAAACG
GAGAAATGCAAATAGGAGTATTTAATACAGAAGATGGATTTAAATATTTTGCTCATCATAATGAAGA
TTTAGGAAATGAAGAAGGTGAAGAAATCTCAGGTGGCTCTGGTAAAATGGTAACAGGAGTATTTAA
AGGACCTAATGGATTTGAGTATTTTGCACCTGCTAATACTCACAATAATAACATAGAAGGTCAGGCT
ATAGTTTACCAGAACAAATTCTTAACTTTGAATGGCAAAAAATATTATTTTGATAATGACTCAAAAG
CAGTTACTGGATGGCAAACCATTGATGGTAAAAAATATTACTTTAATCTTAACACTGCTGAAGCAGC
TACTGGATGGCAAACTATTGATGGTAAAAAATATTACTTTAATCTTAACACTGCTGAAGCAGCTACT
GGATGGCAAACTATTGATGGTAAAAAATATTACTTTAATACTAACACTTTCATAGCCTCAACTGGTTA
TACAAGTATTAATGGTAAACATTTTTATTTTAATACTGATGGTATTATGCAGATAGGAGTGTTTAAAG
GACCTAATGGATTTGAATACTTTGCACCTGCTAATACGGATGCTAACAACATAGAAGGTCAAGCTAT
ACTTTACCAAAATAAATTCTTAACTTTGAATGGTAAAAAATATTACTTTGGTAGTGACTCAAAAGCA
GTTACCGGACTGCGAACTATTGATGGTAAAAAATATTACTTTAATACTAACACTGCTGTTGCAGTTAC
TGGATGGCAAACTATTAATGGTAAAAAATACTACTTTAATACTAACACTTCTATAGCTTCAACTGGTT
ATACAATTATTAGTGGTAAACATTTTTATTTTAATACTGATGGTATTATGCAGATAGGAGTGTTTAAA
GGACCTGATGGATTTGAATACTTTGCACCTGCTAATACAGATGCTAACAATATAGAAGGTCAAGCTA
TACGTTATCAAAATAGATTCCTATATTTACATGACAATATATATTTTGGTAATAATTCAAAAGCG
GCTACTGGTTGGGTAACTATTGATGGTAATAGATATTACTTCGAGCCTAATACAGCTATGGGTGCGA
ATGGTTATAAAACTATTGATAATAAAAATTTTTACTTTAGAAATGGTTTACCTCAGATAGGAGTGTTT
AAAGGGTCTAATGGATTTGAATACTTTGCACCTGCTAATACGGATGCTAACAATATAGAAGGTCAAG
CTATACGTTATCAAAATAGATTCCTACATTTACTTGGAAAATATATTACTTTGGTAATAATTCAAAA
GCAGTTACTGGATGGCAAACTATTAATGGTAAAGTATATTACTTTATGCCTGATACTGCTATGGCTGC
AGCTGGTGGACTTTTCGAGATTGATGGTGTTATATATTTCTTTGGTGTTGATGGAGTAAAAGCCCCTG
GGATATATGGG (SEQ ID NO: 2)

FIG. 11

```
ATGAGTTTAGTTAATAGAAAACAGTTAGAAAAAATGGCAAATGTAAGATTTCGTACTCAAGAAGATGAATATGTTGCAAT
ATTGGATGCTTTAGAAGAATATCATAATATGTCAGAGAATACTGTAGTCGAAAAATATTTAAAATTAAAAGATATAAATA
GTTTAACAGATATTTATATAGATACATATAAAAAATCTGGTAGAAATAAAGCCTTAAAAAAATTTAAGGAATATCTAGTTA
CAGAAGTATTAGAGCTAAAGAATAATAATTTAACTCCAGTTGAGAAAAATTTACATTTTGTTGCGATTGGAGGTCAAATAA
ATGACACTGCTATTAATTATATAAATCAATGGAAAGATGTAAATAGTGATTATAATGTTAATGTTTTTTATGATAGTAATGC
ATTTTTGATAAACACATTGAAAAAAACTGTAGTAGAATCAGCAATAAATGATACACTTGAATCATTTAGAGAAAACTTAA
ATGACCCTAGATTTGACTATAATAAATTCTTCAGAAAACGTATGGAAATAATTTATGATAAACAGAAAAATTTCATAAACT
ACTATAAAGCTCAAAGAGAAGAAAATCCTGAACTTATAATTGATGATATTGTAAAGACATATCTTTCAAATGAGTATTCAA
AGGAGATAGATGAACTTAATACCTATATTGAAGAATCCTTAAATAAAATTACACAGAATAGTGGAAATGATGTTAGAAAC
TTTGAAGAATTTAAAAATGGAGAGTCATTCAACTTATATGAACAAGAGTTGGTAGAAAGGTGGAATTTAGCTGCTGCTTCT
GACATATTAAGAATATCTGCATTAAAAGAAATTGGTGGTATGTATTTAGATGTTAATATGTTACCAGGAATACAACCAGAC
TTATTTGAGTCTATAGAGAAACCTAGTTCAGTAACAGTGGATTTTTGGGAAATGACAAAGTTAGAAGCTATAATGAAATAC
AAAGAATATATACCAGAATATACCTCAGAACATTTTGACATGTTAGACGAAGAAGTTCAAAGTAGTTTTGAATCTGTTCTA
GCTTCTAAGTCAGATAAATCAGAAATATTCTCATCACTTGGTGATATGGAGGCATCACCACTAGAAGTTAAAATTGCATTT
AATAGTAAGGGTATTATAAATCAAGGGCTAATTTCTGTGAAAGACTCATATTGTAGCAATTTAATAGTAAAACAAATCGAG
AATAGATATAAAATATTGAATAATAGTTTAAATCCAGCTATTAGCGAGGATAATGATTTTAATACTACAACGAATACCTTT
ATTGATAGTATAATGGCTGAAGCTAATGCAGATAATGGTAGTATTATGATGGAACTAGGAAAGTATTTAAGAGTTGGTTTC
TTCCCAGATGTTAAAACTACTATTAACTTAAGTGGCCCTGAAGCATATGCGGCAGCTTATCAAGATTTATTAATGTTTAAA
GAAGGCAGTATGAATATCCATTTGATAGAAGCTGATTTAAGAAACTTTGAAATCTCTAAAACTAATATTTCTCAATCAACT
GAACAAGAAATGGCTAGCTTATGGTCATTTGACGATGCAAGAGCTAAAGCTCAATTTGAAGAATATAAAAGGAATTATTT
TGAAGGTTCTCTTGGTGAAGATGATAATCTTGATTTTTCTCAAAATATAGTAGTTGACAAGGAGTATCTTTTAGAAAAAAT
ATCTTCATTAGCAAGAAGTTCAGAGAGAGGATATATACACTATATTGTTCAGTTACAAGGAGATAAAATTAGTTATGAAGC
AGCATGTAACTTATTTGCAAAGACTCCTTATGATAGTGTACTGTTTCAGAAAAATATAGAAGATTCAGAAATTGCATATTA
TTATAATCCTGGAGATGGTGAAATACAAGAAATAGACAAGTATAAAATTCCAAGTATAATTTCTGATAGACCTAAGATTA
AATTAACATTTATTGGTCATGGTAAAGATGAATTTAATACTGATATATTTGCAGGTTTTGATGTAGATTCATTATCCACAGA
AATAGAAGCAGCAATAGATTTAGCTAAAGAGGATATTTCTCCTAAGTCAATAGAAATAAATTTATTAGGAGCTAATATGTT
TAGCTACTCTATCAACGTAGAGGAGACTTATCCTGGAAAATTATTACTTAAAGTTAAAGATAAAATATCAGAATTAATGCC
ATCTATAAGTCAAGACTCTATTATAGTAAGTGCAAATCAATATGAAGTTAGAATAAATAGTGAAGGAAGAAGAGAATTAT
TGGATCATTCTGGTGAATGGATAAATAAAGAAGAAAGTGGTGGCTCTGGTATAACTGGATTTGTGACTGTAGGCGATGAT
AAATACTACTTTAATCCAATTAATGGTGGAGCTGCTTCAATTGGAGAGACAATAATTGATGACAAAAATTATTATTTCAAC
CAAAGTGGAGTGTTACAAACAGGTGTATTTAGTACAGAAGATGGATTTAAATATTTTGCCCCAGCTAATACACTTGATGAA
AACCTAGAAGGAGAAGCAATTGATTTTACTGGAAAATTAATTATTGACGAAAATATTTATTATTTTGATGATAATTATAGA
GGAGCTGTAGAATGGAAAGAATTAGATGGTGAAATGCACTATTTTAGCCCAGAAACAGGTAAAGCTTTTAAAGGTCTAAA
TCAAATAGGTGATTATAAAATACTATTTCAATTCTGATGGAGTTATGCAAAAAGGATTTGTTAGTATAAATGATAATAAACA
CTATTTTGATGATTCTGGTGTTATGAAAGTAGGTTACACTGAAATAGATGGCAAGCATTTCTACTTTGCTGAAAACGGAGA
AATGCAAATAGGAGTATTTAATACAGAAGATGGATTTAAATATTTTGCTCATCATAATGAAGATTTAGGAAATGAAGAAG
GTGAAGAAATCTCAGGTGGCTCTGGTAAAATGGTAACAGGAGTATTTAAAGGACCTAATGGATTTGAGTATTTTGCACCTG
CTAATACTCACAATAATAACATAGAAGGTCAGGCTATAGTTTACCAGAACAAATTCTTAACTTTGAATGGCAAAAAATATT
ATTTTGATAATGACTCAAAAGCAGTTACTTGGCACCTGCTAACAATATCAGAATAATTACTTTAATCTTAACACTGCTG
AAGCAGCTACTGGATGGCAAACTATTGATGGTAAAAAATATTACTTTAATCTTAACACTGCTGAAGCAGCTACTGGATGGC
AAACTATTGATGGTAAAAAATATTACTTTAATACTAACACTTTCATAGCCTCAACTGGTTATACAAGTATTAATGGTAAAC
ATTTTTATTTTAATACTGATGGTATTATGCAGATAGGAGTGTTTAAAGGACCTAATGGATTTGAATACTTTGCACCTGCTAA
TACGGATGCTAACAACATAGAAGGTCAAGCTATACTTTACCAAAATAAATTCTTAACTTTGAATGGTAAAAAATATTACTT
TGGTAGTGACTCAAAAGCAGTTACCGGACTGCGAACTATTGATGGTAAAAAATATTACTTTAATACTAACACTGCTGTTGC
AGTTACTGGATGGCAAACTATTAATGGTAAAAAATACTACTTTAATACTAACACTTCTATAGCTTCAACTGGTTATACAATT
ATTAGTGGTAAACATTTTTATTTTAATACTGATGGTATTATGCAGATAGGAGTGTTTAAAGGACCTGATGGATTTGAATACT
TTGCACCTGCTAATACAGATGCTAACAATATAGAAGGTCAAGCTATACGTTATCAAAATAGATTCCTATATTTACATGACA
ATATATATTATTTTGGTAATAATTCAAAAGCGGCTACTGGTTGGGTAACTATTGATGGTAATAGATATTACTTCGAGCCTAA
TACAGCTATGGGTGCGAATGGTTATAAAACTATTGATAATAAAAATTTTTACTTTAGAAATGGTTTACCTCAGATAGGAGT
GTTTAAAGGGTCTAATGGATTTGAATACTTTGCACCTGCTAATACGGATGCTAACAATATAGAAGGTCAAGCTATACGTTA
TCAAAATAGATTCCTACATTTACTTGGAAAAATATATTACTTTGGTAATAATTCAAAAGCAGTTACTGGATGGCAAACTAT
TAATGGTAAAGTATATTACTTTATGCCTGATACTGCTATGGCTGCAGCTGGTGGACTTTTCGAGATTGATGGTGTTATATAT
TTCTTTGGTGTTGATGGAGTAAAAGCCCCTGGGATATATGGGGGTGGCTCTGGTGCACAAGTCATTAATACAAACAGCCTG
TCGCTGTTGACCCAGAATAACCTGAACAAATCCCAGTCCGCTCTGGGCACCGCTATCGAGCGTCTGTCTTCCGGTCTGCGT
ATCAACAGCGCGAAAGACGATGCGGCAGGTCAGGCGATTGCTAACCGTTTTACCGCGAACATCAAAGGTCTGACTCAGGC
TTCCCGTAACGCTAACGACGGTATCTCCATTGCGCAGACCACTGAAGGCGCGCTGAACGAAATCGACAACAACCTGCAGC
GTGTGCGTGAACTGGCGGTTCAGTCTGCTAACAGCACCAACTCCCAGTCTGACCTCGACTCCATCCAGGCTGAAATCACCC
AGCGCCTGAACGAAATCGACCGTGTATCCGGCCAGACTCAGTTCAACGGCGTGAAAGTCCTGGCGCAGGACAACACCCTG
ACCATCCAGGTTGGTGCCAACGACGGTGAAACTATCGATATCGATCTGAAGCAGATCAACTCTCAGACCCTGGGTCTGGAT
ACGCTGAATGTGCAACAAAAATATAAGGTCAGCGATACGGCTGCAACTGTTACAGGATATGCCGATACTACGATTGCTTTA
GACAATAGTACTTTTAAAGCCTCGGCTACTGGTCTTGGTGGTACTGACCAGAAAATTGATGGCGATTTAAAATTTGATGAT
ACGACTGGAAAATATTACGCCAAAGTTACCGTTACGGGGGGAACTGGTAAAGATGGCTATTATGAAGTTTCCGTTGATAA
GACGAACGGTGAGGTGACTCTTGCTGGCGGTGCGACTTCCCCGCTTACAGGTGGACTACCTGCGACAGCAACTGAGGATG
TGAAAAATGTCCAAGTTGCAAATGCTGATTTGACAGAGGCTAAAGCCGCATTGACAGCAGCAGGTGTTACCGGCACAGCA
TCTGTTGTTAAGATGTCTTATACTGATAATAACGGTAAAACTATTGATGGTGGTTTAGCAGTTAAGGTAGGCGATGATTAC
TATTCTGCAACTCAAAATAAAGATGGTTCCATAAGTATTAATACTACGAAATACACTGCAGATGACGGTACATCCAAAACT
GCACTAAACAAACTGGGTGGCGCAGACGGCAAAACCGAAGTTGTTTCTATTGGTGGTAAAACTTACGCTGCAAGTAAAGC
CGAAGGTCACAACTTTAAAGCACAGCCTGATCTGGCGGAAGCGGCTGCTACAACCACCGAAAACCCGCTGCAGAAAATTG
ATGCTGCTTTGGCACAGGTTGACACGTTACGTTCTGACCTGGGTGCGGTACAGAACCGTTTCAACTCCGCTATTACCAACCT
GGGCAACACCGTAAACAACCTGACTTCTGCCCGTAGCCGTATCGAAGATTCCGACTACGCGACCGAAGTTTCCAACATGTC
TCGCGCGCAGATTCTGCAGCAGGCCGGTACCTCCGTTCTGGCGCAGGCGAACCAGGTTCCGCAAAACGTCCTCTCTTTACT
GCGT (SEQ ID NO: 3)
``` atgagtttagttaatagaaaacagttagaaaaaatggcaaatgtaagatttcgtactcaagaagatgaatatgttgcaatattggatgctttagaagaatat
cataatatgtcagagaatactgtagtcgaaaaatatttaaaattaaaagatataaatagtttaacagatatttatatagatacatataaaaaatctggtagaa
ataaagccttaaaaaaatttaaggaatatctagttacagaagtattagagctaaagaataataatttaactccagttgagaaaaatttacattttgttgcgatt
ggaggtcaaataaatgacactgctattaattatataaatcaatggaaagatgtaaatagtgattataatgttaatgtttttatgatagtaatgcattttgataa
acacattgaaaaaactgtagtagaatcagcaataaatgatacacttgaatcatttagagaaaacttaaatgaccctagatttgactataataaattcttca
gaaaacgtatggaaataatttatgataaacagaaaaatttcataaactactataaagctcaaagagaagaaaatcctgaacttataattgatgatattgtaa
agacatatctttcaaatgagtattcaaaggagatagatgaacttaatacctatattgaagaatccttaaataaaattacacagaatagtggaaatgatgtta
gaaactttgaagaatttaaaaatggagagtcattcaacttatatgaacaagagttggtagaaaaggtggaatttagctgctgcttctgacatattaagaatat
ctgcattaaaagaaattggtggtatgtatttagatgttaatatgttaccaggaatacaaccagacttatttgagtctatagagaaacctagttcagtaacagt
ggattttgggaaatgacaaagttagaagctataatgaaatacaaagaatatataccagaatatacctcagaacattttgacatgttagacgaagaagttc
aaagtagttttgaatctgttctagcttctaagtcagataaatcagaaatattctcatcacttggtgatatggaggcatcaccactagaagttaaaattgcattt
aatagtaagggtattataaatcaaggcgctaatttctgtgaaagactcatattgtagcaatttaatagtaaaacaaatcgagaatagatataaaatattgaata
atagtttaaatccagctattagcgaggataatgattttaatactacaacgaataccttattgatagtataatggctgaagctaatgcagataatggtagattt
atgatggaactaggaaagtatttaagagttggtttcttcccagatgttaaaactactattaacttaagtggccctgaagcatatgcggcagcttatcaagat
ttattaatgtttaaagaaggcagtatgaatatccatttgatagaagctgatttaagaaactttgaaatctctaaaactaatatttctcaatcaactgaacaaga
aatggctagcttatggtcatttgacgatgcaagagctaaagctcaatttgaagaatataaaaggaattattttgaaggttctcttggtgaagatgataatctt
gattttctcaaaatatagtagttgacaaggagtatctttagaaaaaatatcttcattagcaagaagttcagagagaggatatatacactatattgttcagtt
acaaggagataaaattagttatgaagcagcatgtaacttatttgcaaagactcct tatgatagtgtactgtttcagaaaaatatagaagattcagaaattgc
atattattataatcctggagatggtgaaatacaagaaatagacaagtataaaattccaagtataatttctgatagacctaagattaaattaacatttattggtc
atggtaaagatgaatttaatactgatatatttgcaggttttgatgtagattcattatccacagaaatagaagcagcaatagatttagctaaagaggatatttct
cctaagtcaatagaaataaatttattaggagctaatatgtttagctactctatcaacgtagaggagacttatcctggaaaattattacttaaagttaaagata
aaatatcagaattaatgccatctataagtcaagactctattatagtaagtgcaaatcaatatgaagttagaataaatagtgaaggaagaagagaattattg
gatcattctggtgaatggataaataaagaagaaagtggtggctctggtaaaatggtaacaggagtatttaaaggacctaatggatttgagtattttgcacc
tgctaatactcacaataataacatagaaggtcaggctatagtttaccagaacaaattcttaactttgaatggcaaaaaatattattttgataatgactcaaaa
gcagttactggatggcaaaccattgatggtaaaaaatattactttaatcttaacactgctgaagcagctactggatggcaaactattgatggtaaaaaata
ttactttaatcttaacactgctgaagcagctactggatggcaaactattgatggtaaaaaatattacttaatactaacactttcatagcctcaactggttata
caagtattaatggtaaacatttttatttaatactgatggtattatgcagataggagtgtttaaaggacctaatggatttgaatactttgcacctgctaatacgg
atgctaacaacatagaaggtcaagctatactttaccaaaatattcttaactttgaatggtaaaaaatattactttggtagtgactcaaaagcagttaccg
gactgcgaactattgatggtaaaaaatattactttaatactaacactgctgttgcagttactggatggcaaactattaatggtaaaaaatactactttaatact
aacacttctatagcttcaactggttatacaattattagtggtaaacattttatttaatactgatggtattatgcagataggagtgtttaaaggacctgatggat
ttgaatactttgcacctgctaatacagatgctaacaatatagaaggtcaagctatacgttatcaaaatagattcctatatttacatgacaatatatattatttg
gtaataattcaaaagcggctactggttgggtaactattgatggtaatagatattacttcgagcctaatacagctatgggtgcgaatggttataaaactattg
ataataaaaattttttactttagaaatggtttacctcagataggagtgtttaaagggtctaatggatttgaatactttgcacctgctaatacggatgctaacaat
atagaaggtcaagctatacgttatcaaaatagattcctacatttacttggaaaaatatattactttggtaataattcaaaagcagttactggatggcaaacta
ttaatggtaaagtatattactttatgcctgatactgctatggctgcagctggtggacttttcgagattgatggtgttatatattcttt ggtgttgatggagtaaa
agcccctgggatatatgggggtggctctggtgcacaagtcattaatacaaacagcctgtcgctgttgacccagaataacctgaacaaatcccagtccg
ctctgggcaccgctatcgagcgtctgtcttccggtctgcgtatcaacagcgcgaaagacgatgcggcaggtcaggcgattgctaaccgttttaccgcg
aacatcaaaggtctgactcaggcttcccgtaacgctaacgacggtatctccattgcgcagaccactgaaggcgcgctgaacgaaatcaacaacaacc
tgcagcgtgtgcgtgaactggccggttcagtctgctaacagcaccaactcccagtctgacctcgactccatccaggctgaaatcacccagcgcctgaa
cgaaatcgaccgtgtatccggccagactcagttcaacggcgtgaaagtcctggcgcaggacaacaccctgaccatccaggttggtgccaacgacg
gtgaaactatcgatatcgatctgaagcagatcaactctcagaccctgggtctggatacgctgaatgtgcaacaaaaatataaggtcagcgatacggct
gcaactgttacaggatatgccgatactacgattgctttagacaatagtacttttaaagcctcggctactggtcttggtggtactgaccagaaaattgatgg
cgatttaaaatttgatgatacgactggaaaatattacgccaaagttaccgttacgggggggaactggtaaagatggctattatgaagtttccgttgataaga
cgaacggtgaggtgactcttgctggcggtgcgacttccccgcttacaggtggactacctgcgacagcaactgaggatgtgaaaaatgtccaagttgc
aaatgctgatttgacagaggctaaagccgcattgacagcagcaggtgttaccggcacagcatctgttgttaagatgtcttatactgataataacggtaaa
actattgatggtggtttagcagttaaggtaggcgatgattactattctgcaactcaaaataaagatggttccataagtattaatactacgaaatacactgca
gatgacggtacatccaaaactgcactaaacaaactgggtggcgcagacggcaaaaccgaagttgtttctattggtggtaaaacttacgctgcaagtaa
agccgaaggtcacaactttaaagcacagcctgatctggcggaagcggctgctacaaccaccgaaaacccgctgcagaaaattgatgctgctttggc
acaggttgacacgttacgttctgacctgggtgcggtacagaaccgtttcaactccgctattaccaacctgggcaacaccgtaaacaacctgacttctgc
ccgtagccgtatcgaagattccgactacgcgaccgaagtttccaacatgtctcgcgcgcagattctgcagcaggccggtacctccgttctggcgcag
gcgaaccaggttccgcaaaacgtcctctctttactgcgt (SEQ ID NO: 4)

aa sequence (1417 aa) for Tcd169

MSLVNRKQLEKMANVRFRTQEDEYVAILDALEEYHNMSENTVVEKYLKLKDINSLTDIYIDTYKKSGRNKALKKFKEYLVT
EVLELKNNNLTPVEKNLHFVAIGGQNDTAINYINQWKDVNSDYNVNVFYDSNAFLINTLKKTVVESAINDTLESFRENL
NDPRFDYNKFFRKRMEIIYDKQKNFINYYKAQREENPELIIDDIVKTYLSNEYSKEIDELNTYIEESLNKITQNSGNDVRNFE
EFKNGESFNLYEQELVERWNLAAASDILRISALKEIGGMYLDVNMLPGIQPDLFESIEKPSSVTVDFWEMTKLEAIMKYK
EYIPEYTSEHFDMLDEEVQSSFESVLASKSDKSEIFSSLGDMEASPLEVKIAFNSKGIINQGLISVKDSYCSNLIVKQIENRYK
ILNNSLNPAISEDNDFNTTTNTFIDSIMAEANADNGRFMMELGKYLRVGFFPDVKTTINLSGPEAYAAAYQDLLMFKEG
SMNIHLIEADLRNFEISKTNISQSTEQEMASLWSFDDARAKAQFEEYKRNYFEGSLGEDDNLDFSQNIVVDKEYLLEKISS
LARSSERGYIHYIVQLQGDKISYEAACNLFAKTPYDSVLFQKNIEDSEIAYYYNPGDGEIQEIDKYKIPSISDRPKIKLTFIGH
GKDEFNTDIFAGFDVDSLSTEIEAAIDLAKEDISPKSIEINLLGANMFSYSINVEETYPGKLLLKVKDKISELMPSISQDSIIVS
ANQYEVRINSEGRRELLDHSGEWINKEESGGSGITGFVTVGDDKYYFNPINGGAASIGETIIDDKNYYFNQSGVLQTGVF
STEDGFKYFAPANTLDENLEGEAIDFTGKLIIDENIYYFDDNYRGAVEWKELDGEMHYFSPETGKAFKGLNQIGDYKYYF
NSDGVMQKGFVSINDNKHYFDDSGVMKVGYTEIDGKHFYFAENGEMQIGVFNTEDGFKYFAHHNEDLGNEEGEEIS
GGSGKMVTGVFKGPNGFEYFAPANTHNNNIEGQAIVYQNKFLTLNGKKYYFDNDSKAVTGWQTIDGKKYYFNLNTAE
AATGWQTIDGKKYYFNLNTAEAATGWQTIDGKKYYFNTNTFIASTGYTSINGKHFYFNTDGIMQIGVFKGPNGFEYFAP
ANTDANNIEGQAILYQNKFLTLNGKKYYFGSDSKAVTGLRTIDGKKYYFNTNTAVAVTGWQTINGKKYYFNTNTSIAST
GYTIISGKHFYFNTDGIMQIGVFKGPDGFEYFAPANTDANNIEGQAIRYQNRFLYLHDNIYYFGNNSKAATGWVTIDGN
RYYFEPNTAMGANGYKTIDNKNFYFRNGLPQIGVFKGSNGFEYFAPANTDANNIEGQAIRYQNRFLHLLGKIYYFGNNS
KAVTGWQTINGKVYYFMPDTAMAAAGGLFEIDGVIYFFGVDGVKAPGIYG (SEQ ID NO: 5)

FIG. 14 aa sequence (1915 aa) for Tcd169FI

MSLVNRKQLEKMANVRFRTQEDEYVAILDALEEYHNMSENTVVEKYLKLKDINSLTDIYIDTYKKSGRNKALKKFKEYLVT
EVLELKNNNLTPVEKNLHFVAIGGQNDTAINYINQWKDVNSDYNVNVFYDSNAFLINTLKKTVVESAINDTLESFRENL
NDPRFDYNKFFRKRMEIIYDKQKNFINYYKAQREENPELIIDDIVKTYLSNEYSKEIDELNTYIEESLNKITQNSGNDVRNFE
EFKNGESFNLYEQELVERWNLAAASDILRISALKEIGGMYLDVNMLPGIQPDLFESIEKPSSVTVDFWEMTKLEAIMKYK
EYIPEYTSEHFDMLDEEVQSSFESVLASKSDKSEIFSSLGDMEASPLEVKIAFNSKGIINQGLISVKDSYCSNLIVKQIENRYK
ILNNSLNPAISEDNDFNTTTNTRDSIMAEANADNGRFMMELGKYLRVGFFPDVKTTINLSGPEAYAAAYQDLLMFKEG
SMNIHLIEADLRNFEISKTNISQSTEQEMASLWSFDDARAKAQFEEYKRNYFEGSLGEDDNLDFSQNIVVDKEYLLEKISS
LARSSERGYIHYIVQLQGDKISYEAACNLFAKTPYDSVLFQKNIEDSEIAYYYNPGDGEIQEIDKYKIPSISDRPKIKLTFIGH
GKDEFNTDIFAGFDVDSLSTEIEAAIDLAKEDISPKSIEINLLGANMFSYSINVEETYPGKLLLKVKDKISELMPSISQDSIIVS
ANQYEVRINSEGRRELLDHSGEWINKEESGGSGITGFVTVGDDKYYFNPINGGAASIGETIIDDKNYYFNQSGVLQTGVF
STEDGFKYFAPANTLDENLEGEAIDFTGKLIIDENIYYFDDNYRGAVEWKELDGEMIHYFSPETGKAFKGLNQIGDYKYYF
NSDGVMQKGFVSINDNKHYFDDSGVMIKVGYTEIDGKHFYFAENGEMQIGVFNTEDGFKYFAHHNEDLGNEEGEEIS
GGSGKMVTGVFKGPNGFEYFAPANTHNNNIEGQAIVYQNKFLTLNGKKYYFDNDSKAVTGWQTIDGKKYYFNLNTAE
AATGWQTIDGKKYYFNLNTAEAATGWQTIDGKKYYFNTNTFIASTGYTSINGKHFYFNTDGIMQIGVFKGPNGFEYFAP
ANTDANNIEGQAILYQNKFLTLNGKKYYFGSDSKAVTGLRTIDGKKYYFNTNTAVAVTGWQTINGKKYYFNTNTSIAST
GYTIISGKHFYFNTDGIMQIGVFKGPDGFEYFAPANTDANNIEGQAIRYQNRFLYLHDNIYYFGNNSKAATGWVTIDGN
RYYFEPNTAMGANGYKTIDNKNFYFRNGLPQIGVFKGSNGFEYFAPANTDANNIEGQAIRYQNRFLHLLGKIYYFGNNS
KAVTGWQTINGKVYYFMPDTAMAAAGGLFEIDGVIYFFGVDGVKAPGIYGGGSGAQVINTNSLSLLTQNNLNKSQSAL
GTAIERLSSGLRINSAKDDAAGQAIANRFTANIKGLTQASRNANDGISIAQTTEGALNEINNNLQRVRELAVQSANSTNS
QSDLDSIQAEITQRLNEIDRVSGQTQFNGVKVLAQDNTLTIQVGANDGETIDIDLKQINSQTLGLDTLNVQQKYKVSDT
AATVTGYADTTIALDNSTFKASATGLGGTDQKIDGDLKFDDTTGKYYAKVTVTGGTGKDGYYEVSVDKTNGEVTLAGG
ATSPLTGGLPATATEDVKNVQVANADLTEAKAALTAAGVTGTASVVKMSYTDNNGKTIDGGLAVKVGDDYYSATQNK
DGSISINTTKYTADDGTSKTALNKLGGADGKTEVVSIGGKTYAASKAEGHNFKAQPDLAEAAATTTENPLQKIDAALAQ
VDTLRSDLGAVQNRFNSAITNLGNTVNNLTSARSRIEDSDYATEVSNMSRAQILQQAGTSVLAQANQVPQNVLSLLR (SEQ ID NO: 6)

FIG. 15 aa sequence (1708 aa) for Tcd138FI

MSLVNRKQLEKMANVRFRTQEDEYVAILDALEEYHNMSENTVVEKYLKLKDINSLTDIYIDTYKKSGRNKALKKFKEYLVT
EVLELKNNNLTPVEKNLHFVAIGGQINDTAINYINQWKDVNSDYNVNVFYDSNAFLINTLKKTVVESAINDTLESFRENL
NDPRFDYNKFFRKRMEIIYDKQKNFINYYKAQREENPELIDDIVKTYLSNEYSKEIDELNTYIEESLNKITQNSGNDVRNFE
EFKNGESFNLYEQELVERWNLAAASDILRISALKEIGGMYLDVNMLPGIQPDLFESIEKPSSVTVDFWEMTKLEAIMKYK
EYIPEYTSEHFDMLDEEVQSSFESVLASKSDKSEJFSSLGDMEASPLEVKIAFNSKGIINQGLISVKDSYCSNLIVKQIENRYK
ILNNSLNPAISEDNDFNTTTNTFIDSIMAEANADNGRFMMELGKYLRVGFFPDVKTTINLSGPEAYAAAYQDLLMFKEG
SMNIHLIEADLRNFEISKTNISQSTEQEMASLWSFDDARAKAQFEEYKRNYFEGSLGEDDNLDFSQNIVVDKEYLLEKISS
LARSSERGYIHYIVQLQGDKISYEAACNLFAKTPYDSVLFQKNIEDSEIAYYYNPGDGEIQEIDKYKIPSIISDRPKIRLTFIGH
GKDEFNTDIFAGFDVDSLSTEIEAAIDLAKEDISPKSIEINLLGANMFSYSINVEETYPGKLLLKVKDKISELMPSISQDSIIVS
ANQYEVRIINSEGRRELLDHSGEWINKEESGGSGKMVTGVFKGPNGFEYFAPANTHNNNIEGQAIVYQNKFLTLNGKKY
YFDNDSKAVTGWQTIDGKKYYFNLNTAEAATGWQTIDGKKYYFNLNTAEAATGWQTIDGKKYYFNTNTFIASTGYTSI
NGKHFYFNTDGIMQIGVFKGPNGFEYFAPANTDANNIEGQAILYQNKFLTLNGKKYYFGSDSKAVTGLRTIDGKKYYFN
TNTAVAVTGWQTINGKKYYFNTNTSIASTGYTIISGKHFYFNTDGIMQIGVFKGPDGFEYFAPANTDANNIEGQAIRYQ
NRFLYLHDNIYYFGNNSKAATGWVTIDGNRYYFEPNTAMGANGYKTIDNKNFYFRNGLPQIGVFKGSNGFEYFAPANT
DANNIEGQAIRYQNRFLHLLGKIYYFGNNSKAVTGWQTINGKVYYFMPDTAMAAAGGLFEIDGVIYFFGVDGVKAPGI
YGGGSGAQVINTNSLSLLTQNNLNKSQSALGTAIERLSSGLRINSAKDDAAGQAIANRFTANIKGLTQASRNANQGISIA
QTTEGALNEINNNLQRVRELAVQSANSTNSQSDLDSIQAEITQRLNEIDRVSGQTQFNGVKVLAQDNTLTIQVGANDG
ETIDIDLKQINSQTLGLDTLNVQQKYKVSDTAATVTGYADTTIALDNSTFKASATGLGGTDQKIDGDLKFDDTTGKYYAK
VTVTGGTGKDGYYEVSVDKTNGEVTLAGGATSPLTGGLPATATEDVKNIVQVANADLTEAKAALTAAGVTGTASVVKM
SYTDNNGKTIDGGLAVKVGDDYYSATQNKDGSISINTTKYTADDGTSKTALNKLGGADGKTEVVSIGGKTYAASKAEGH
NFKAQPDLAEAAATTTENPLQKIDAALAQVDTLRSDLGAVQNRFNSAITNLGNTVNNLTSARSRIEDSDYATEVSNMGR
AQILQQAGTSVLAQANQVPQNVLSLLR (SEQ ID NO: 7)

FIG. 16

IMMUNOGENIC PROTEINS AGAINST CLOSTRIDIUM DIFFICILE

CROSS-REFERENCE TO RELATED APPLICATION(S)

This application is a continuation application of U.S. patent application Ser. No. 15/992,497, filed on May 30, 2018, which claims priority to U.S. Provisional Patent Application No. 62/513,247, filed on May 31, 2017, the entire contents of which are fully incorporated herein by reference.

STATEMENT OF GOVERNMENT SUPPORT

This invention was made with government support under Grant Numbers R21 AI113470 and K01 DK092352 awarded by the National Institutes of Health. The government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 64,312 Bytes ASCII (Text) file named "17A057PRC-210112-9062-US02_ST25.txt", created on May 29, 2018.

TECHNICAL FIELD

The present disclosure relates to immunogenic proteins and methods for treating and/or preventing infections caused by *Clostridium difficile*.

BACKGROUND

*Clostridium difficile* is a spore-forming anaerobic and toxin-producing *bacillus*. It is the most common cause of nosocomial antibiotic-associated diarrhea. A CDC study estimated that 29,000 deaths were caused by *Clostridium difficile* in the U.S. in 2011. Antibiotic treatment of *Clostridium difficile* infections may be difficult, due both to antibiotic resistance and physiological factors of the bacteria (e.g., spore formation and protective effects of the pseudomembrane). Accordingly, there exists a need for effective therapies and prevention of infections caused by *Clostridium difficile*.

SUMMARY OF THE INVENTION

In one aspect, disclosed is an immunogenic protein that comprises the glucosyltranferase domain of *Clostridium difficile* toxin TcdB, the cysteine proteinase domain of *Clostridium difficile* toxin TcdB, and the receptor binding domain of *Clostridium difficile* toxin TcdA. Also disclosed is an immunogenic protein comprising the glucosyltranferase domain of *Clostridium difficile* toxin TcdB, the cysteine proteinase domain of *Clostridium difficile* toxin TcdB, the receptor binding domain of *Clostridium difficile* toxin TcdA, and the receptor binding domain of *Clostridium difficile* toxin TcdB. Also disclosed is an immunogenic protein comprising the glucosyltranferase domain of *Clostridium difficile* toxin TcdB, the cysteine proteinase domain of *Clostridium difficile* toxin TcdB, the receptor binding domain of *Clostridium difficile* toxin TcdA, the receptor binding domain of *Clostridium difficile* toxin TcdB, and *Salmonella typhimurium* flagellin. Also disclosed is an immunogenic protein comprising the glucosyltranferase domain of *Clostridium difficile* toxin TcdB, the cysteine proteinase domain of *Clostridium difficile* toxin TcdB, and the receptor binding domain of *Clostridium difficile* toxin TcdA, and *Salmonella typhimurium* flagellin. The immunogenic proteins may comprise a W102A amino acid substitution and a D288N amino acid substitution in the glucosyltransferase domain. The immunogenic proteins may comprise a C698A amino acid substitution in the cysteine proteinase domain. The disclosed immunogenic proteins may lack a transmembrane domain.

Further disclosed are compositions comprising the disclosed immunogenic proteins against *Clostridium difficile*. Also disclosed are methods of treating *Clostridium difficile* bacterial infection in a subject. The method may comprise administering to the subject an effective amount of the disclosed immunogenic proteins or compositions comprising the same.

BRIEF DESCRIPTION OF THE DRAWINGS

FIGS. 1A-1D show the domains of TcdA and TcdB and construction of Tcd169, Tcd169Fl, and Tcd138Fl. Brackets are used to indicate domains that are connected by a GGSG linker (SEQ ID NO: 1). FIG. 1A shows the domains of TcdA and TcdB. FIG. 1B shows construction of Tcd169 (SEQ ID NO: 5), of which the GT of TcdB and the CPD of TcdB (SEQ ID NO: 8), the RBD of TcdB (SEQ ID NO: 10) and the RBD of TcdA (SEQ ID NO: 9) are connected by GGSG linkers. FIG. 1C shows construction of Tcd169Fl (SEQ ID NO: 6), of which the GT of TcdB and the CPD of TcdB (SEQ ID NO: 8), the RBD of TcdB (SEQ ID NO: 10), the RBD of TcdA (SEQ ID NO: 9) and the sFLiC (SEQ ID NO: 11) are connected by GGSG linkers. FIG. 1D shows construction of Tcd138Fl (SEQ ID NO: 7), of which the GT of TcdB and the CPD of TcdB (SEQ ID NO: 8), the RBD of TcdA (SEQ ID NO: 9) and the sFLiC (SEQ ID NO: 11) are connected by GGSG linkers.

FIG. 11 shows the nucleotide sequence that encodes for Tcd169 (4251 bp) (SEQ ID NO.: 2).

FIG. 12 shows the nucleotide sequence that encodes for Tcd169Fl (5745 bp) (SEQ ID NO.: 3).

FIG. 13 shows the nucleotide sequence that encodes for Tcd138Fl (5124 bp) (SEQ ID NO.: 4).

FIG. 14 shows the amino acid sequence for Tcd169 (SEQ ID NO.: 5).

FIG. 15 shows the amino acid sequence for Tcd169Fl (SEQ ID NO.: 6).

FIG. 16 shows the amino acid sequence for Tcd138Fl (SEQ ID NO.: 7).

DETAILED DESCRIPTION

Figure 2:
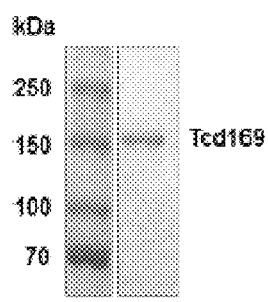
FIG. 2 shows the expression and purification of Tcd169.

Disclosed herein are immunogenic proteins and compositions useful for the treatment or prevention of bacterial infections. The bacterial infection may be caused by *Clostridium difficile*. The disclosed immunogenic proteins and compositions may be used to prevent a *Clostridium difficile* infection in a subject. The disclosed immunogenic proteins and compositions may be used to treat a *Clostridium difficile* infection in a subject. Methods of treating and/or preventing a *Clostridium difficile* infection are disclosed.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The terms "administration" or "administering" as used herein may include the process in which the immunogenic proteins and compositions as described herein are delivered to a subject. The immunogenic proteins and compositions may be administered in various routes including, but not limited to, oral, mucosal, mucosal nasal, parenteral (including intravenous, intra-arterial, and other appropriate parenteral routes), intrathecally, intramuscularly, subcutaneously, colonically, rectally, and nasally, transcutaneously, among others. The dosing of the immunogenic proteins and compositions described may be determined by the circumstances of the subject, as known in the art. The dosing of a subject herein may be accomplished through individual or unit doses of the immunogenic proteins and compositions herein or by a combined or prepackaged or pre-formulated dose.

Administration may depend upon the amount of immunogenic protein or composition administered, the number of doses, duration of treatment, and the like. For example, multiple doses of the immunogenic protein or composition may be administered to the subject. The frequency of administration of the immunogenic protein or composition may vary depending on any of a variety of factors. The duration of administration of the immunogenic protein or composition, e.g., the period of time over which the immunogenic protein or composition is administered, may vary, depending on any of a variety of factors, including subject response, etc.

The amount of the immunogenic proteins and compositions administered may vary according to factors such as the degree of susceptibility of the individual, the age, sex, and weight of the individual, idiosyncratic responses of the individual, the dosimetry, and the like. Detectably effective amounts of the immunogenic protein or composition of the present disclosure may also vary.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

The terms "*Clostridium difficile*", "*C. difficile, C. diff*", and "CDF", and "cdf" as used herein, may be used interchangeably.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The terms "composition", "compositions", "pharmaceutical composition", and "pharmaceutical compositions" are used interchangeably herein to refer to a composition comprising an immunogenic protein disclosed herein.

The term "immunogen", as used herein refers to any substance that may be specifically bound by components of the immune system.

The term "parenterally," as used herein, refers to modes of administration which include intravenous, intramuscular, intraperitoneal, intrasternal, subcutaneous and intraarticular injection and infusion.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and includes an excipient, diluent, carrier, and adjuvant that are acceptable for veterinary use and/or human pharmaceutical use.

As used herein, the term "subject," "patient," or "organism" includes humans and mammals (e.g., mice, rats, pigs, cats, dogs, and horses). Typical subjects to which an agent(s) of the present disclosure may be administered may include mammals, particularly primates, especially humans. For veterinary applications, suitable subjects may include, for example, livestock such as cattle, sheep, goats, cows, swine, and the like; poultry such as chickens, ducks, geese, turkeys, and the like; and domesticated animals particularly pets such as dogs and cats. For diagnostic or research applications, suitable subjects may include mammals, such as rodents (e.g., mice, rats, hamsters), rabbits, primates, and swine such as inbred pigs and the like. The subject may have a bacterial infection. The subject may have a bacterial infection caused by *Clostridium difficile*. The subject may be taking antibiotics. The subject may be taking antibiotics for a bacterial infection that is caused by bacteria other than *Clostridium difficile*. The subject may be at risk for an infection caused by *Clostridium difficile*.

A "therapeutically effective amount" or "effective amount" as used interchangeably herein, refers to an amount effective, at dosages and for periods of time necessary, to achieve the desired therapeutic result. A therapeutically effective amount of the immunogenic protein or composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of immunogenic proteins and compositions of the disclosure are outweighed by the therapeutically beneficial effects. The term "toxin" as used herein, may refer to small molecules, peptides, or proteins that are capable of causing disease on contact with or absorption by body tissues interacting with biological macromolecules such as enzymes or cellular receptors. Toxins may be produced by microorganisms. Toxins may be produced by *Clostridium difficile*. Toxins may be virulence determinants responsible for microbial pathogenicity. Toxins may be virulence determinants responsible for evasion of the host immune response.

"Treat," "treatment," or "treating," means preventing, suppressing, repressing, ameliorating, or completely eliminating a pathological condition. For example, the pathological condition may be a bacterial infection caused by *Clostridium difficile*. Preventing the pathological condition involves administering an immunogenic protein or composition of the present invention to a subject prior to onset of the pathological condition. For example, preventing *Clostridium difficile* infection may involve administering the immunogenic protein or composition of the present invention to a subject prior to onset of the infection. Repressing or ameliorating the pathological condition involves administering an immunogenic protein or composition of the present invention to a subject after clinical appearance of the pathological condition. For example, repressing or ameliorating *Clostridium difficile* infection may involve administering an immunogenic protein or composition of the present invention after onset of symptoms of *Clostridium difficile* infection. Administration of the immunogenic proteins or compositions of the present invention may improve or prevent one or more symptoms associated with the pathological condition. For example, administration of the immunogenic proteins or compositions of the present invention may improve or prevent one or more symptoms associated with *Clostridium difficile* infection. Symptoms include, but are not limited to, watery diarrhea, fever, loss of appetite, nausea, abdominal pain/tenderness.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. IMMUNOGENIC PROTEINS AGAINST *CLOSTRIDIUM DIFFICILE*

In one aspect, disclosed are immunogenic proteins against *Clostridium difficile*. The immunogenic protein may be a chimeric protein. The immunogenic protein may comprise one or more domains from *Clostridium difficile* toxins. The immunogenic protein may comprise one or more domains from *Clostridium difficile* toxin A (TcdA). The immunogenic protein may comprise the glucosyltransferase domain (GT) from TcdA. The immunogenic protein may comprise the cysteine proteinase domain (CPD) from TcdA. The immunogenic protein may comprise the receptor binding domain (RBD) from TcdA. The immunogenic protein may contain one or more domains from *Clostridium difficile* toxin B (TcdB). The immunogenic protein may comprise the glucosyltransferase domain from TcdB. The immunogenic protein may comprise the cysteine proteinase domain from TcdB.

The immunogenic protein may comprise the receptor binding domain from TcdB. The immunogenic protein may lack a transmembrane domain.

The immunogenic protein may contain one or more domains from *Salmonella typhimurium*. The immunogenic protein may contain *Salmonella typhimurium* flagellin. For example, the immunogenic protein may contain sFliC.

The one or more domains may be connected by an amino acid linker. Any combination of one or more domains may be connected by an amino acid linker. For example, the CPD of TcdB and the RBD of TcdB may be connected by an amino acid linker. As another example, the CPD of TcdB and the RBD of TcdA may be connected by an amino acid linker. The RBD of TcdB and the RBD of TcdA may be connected by an amino acid linker. The TBD of TcdA and sFliC may be connected by an amino acid linker. The amino acid linker may be the amino acid sequence GGSG as set forth in SEQ ID NO.: 1.

The immunogenic proteins may comprise one or more mutations. The one or more mutations may reduce the toxicity of the immunogenic protein. The one or more mutations may render the immunogenic protein atoxic. For example, the immunogenic protein may comprise one or more amino acid substitutions. For example, the immunogenic protein may comprise a W102A amino acid substitution and a D288N amino acid substitution in the GT of TcdB. The immunogenic protein may comprise a C698A amino acid substitution in the CPD of TcdB. The immunogenic protein may comprise a W102A amino acid substitution and a D288N amino acid substitution in the GT of TcdB and a C698A amino acid substitution in the CPD of TcdB.

The immunogenic protein may comprise the glucosyltransferase domain of TcdB, cysteine proteinase domain of TcdB, receptor binding domain of TcdB, and the receptor binding domain of TcdA. The immunogenic protein may comprise a W102A amino acid substitution and a D288N amino acid substitution in the GT of TcdB. The immunogenic protein may comprise a C698A amino acid substitution in the CPD of TcdB. The immunogenic protein may comprise a W102A amino acid substitution and a D288N amino acid substitution in the GT of TcdB and a C698A amino acid substitution in the CPD of TcdB. The immunogenic protein may be encoded by the nucleotide sequence as set forth in SEQ ID NO.: 2. The immunogenic protein may be Tcd169 (SEQ ID NO.: 5).

The immunogenic protein may comprise the glucosyltransferase domain of TcdB, cysteine proteinase domain of TcdB, receptor binding domain of TcdB, the receptor binding domain of TcdA, and flagellin of *Salmonella typhimurium*. The immunogenic protein may comprise a W102A amino acid substitution and a D288N amino acid substitution in the GT of TcdB. The immunogenic protein may comprise a C698A amino acid substitution in the CPD of TcdB. The immunogenic protein may comprise a W102A amino acid substitution and a D288N amino acid substitution in the GT of TcdB and a C698A amino acid substitution in the CPD of TcdB. The immunogenic protein may be encoded by the nucleotide sequence as set forth in SEQ ID NO.: 3. The immunogenic protein may be Tcd169Fl (SEQ ID NO: 6).

In some embodiments, the immunogenic protein comprises the glucosyltransferase domain of TcdB, the cysteine proteinase domain of TcdB, the receptor binding domain (RBD) of TcdA, and flagellin of *Salmonella typhimurium*. The immunogenic protein may comprise a W102A amino acid substitution and a D288N amino acid substitution in the GT of TcdB. The immunogenic protein may comprise a C698A amino acid substitution in the CPD of TcdB. The immunogenic protein may comprise a W102A amino acid substitution and a D288N amino acid substitution in the GT of TcdB and a C698A amino acid substitution in the CPD of TcdB. The immunogenic protein may be encoded by the nucleotide sequence as set forth in SEQ ID NO.: 4. The immunogenic protein may be Tcd138Fl (SEQ ID NO.: 7).

The immunogenic proteins may induce a humoral immune response. The immunogenic proteins may induce a cell-mediated immune response.

3. PHARMACEUTICAL COMPOSITIONS

The disclosed immunogenic proteins may be incorporated into pharmaceutical compositions suitable for administration to a subject. The pharmaceutical composition may include a therapeutically effective amount of the immunogenic protein. For example, a therapeutically effective amount of the immunogenic protein may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical composition may further comprise one or more *Clostridium difficile* immunogens. For example, the composition may further comprise one or more *Clostridium difficile* surface proteins. For example, the composition may comprise Cwp84.

The pharmaceutical composition may include one or more pharmaceutically acceptable carriers. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The route by which the disclosed pharmaceutical compositions are administered and the form of the pharmaceutical composition will dictate the type of carrier to be used. The pharmaceutical composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, transdermal, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmelose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, Pa.) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of active and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmelose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound, and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT coatings (available from Rohm & Haas G.M.B.H. of Darmstadt, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid compositions, which may be administered orally, may include a disclosed immunogenic proteins and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed immunogenic proteins and compositions may be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. The carrier of the topical composition preferably aids penetration of the compounds into the skin. The carrier may further include one or more optional components. Transdermal administration may be used to facilitate delivery.

The amount of the carrier employed in conjunction with a disclosed compound is sufficient to provide a practical quantity of composition for administration per unit dose of the medicament. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, *arachis* oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

The pharmaceutical composition may comprise synthetic oligodeoxynucleotides (ODNs). The synthetic oligonucleotides may comprise unmethylated CpG motifs (CpG ODNs) trigger cells that express Toll-like receptor 9 to mount an innate immune response. CpG ODNs may improve the function of professional antigen-presenting cells. CpG ODNs may boost the generation of humoral and cellular immune responses.

4. METHOD OF TREATING BACTERIAL INFECTION

The disclosed immunogenic proteins and compositions may be used a method of treating a bacterial infection in a subject. For example, the disclosed immunogenic proteins and compositions may be used in a method of treating a *Clostridium difficile* infection in a subject. The method may comprise administering to a subject in need thereof an immunogenic protein or a composition disclosed herein. The subject may be diagnosed with or at risk of developing a *Clostridium difficile* infection.

a. Bacterial Infections

The disclosed immunogenic proteins and compositions may be used to treat any bacterial infection in a subject. The disclosed immunogenic proteins and compositions may be administered to a subject who is at risk of developing a bacterial infection or is diagnosed with a bacterial infection. Bacterial infections can affect multiple organs and body systems including, but not limited to, gastrointestinal tract, intestines, skin, mucous membranes, blood, lungs, kidneys, urinary tract, eyes, heart, meninges, respiratory tract, genitals, stomach, bone, connective tissue, and tissue surrounding organs. Bacterial infections may affect more than one organ or body system. Bacterial infections may be systemic. Bacterial infections may be asymptomatic. Bacterial infections may cause a variety of symptoms including, but not limited to, fever, inflammation, wounds that do not heal, weeping wounds, skin rash, red bumps on the skin, abscesses, swollen lymph nodes, nausea, diarrhea, headaches, earaches, sore throat, fatigue, low blood pressure, hyperventilation, weak and rapid pulse, local or systemic pain, and muscle aches. Bacterial infections may cause death. Subjects with co-morbidities or a compromised immune system may be more susceptible to bacterial infections.

The bacterial infection in a subject may be diagnosed prior to treatment with the disclosed immunogenic proteins and compositions. The diagnosis of a bacterial infection may include, but are not limited to, symptomatic diagnostics, microbial culture, microscopy, biochemical tests, PCR based diagnostics, and metagenomics sequencing. A microbial examination may include sample collection, microbial cultivation, identification, and test of antibiotic susceptibility. The diagnosis may include gram staining of the bacterial culture. The diagnosis may include a coagulase test of the bacterial culture. The diagnosis may include a catalase test of the bacterial culture. The diagnosis may include blood tests. The blood tests may include, but are not limited to, a full blood count, measurement of C-reactive protein, measurement of procalcitonin, and measurement of rapid plasma reagin. The diagnosis may include ELISA. The diagnosis may include PCR. The sample may be grown on an agar plate. The sample may be grown in nutrient broth. The growth conditions may include varying factors (e.g., type of growth medium, nutrients, selective compounds, antibiotics, temperature, pH level, oxygen level) to determine the type of bacteria growing. The determination of bacteria growing on an agar plate or in a nutrient broth may determine the bacteria responsible for the subject's infection. Discs containing antibiotic compounds may be placed on the agar plates. The antibiotic compounds may kill the bacteria growing on the plate. The antibiotics that are effective at killing the bacteria may aid in diagnosing the type of bacterial infection.

Samples for diagnosing a bacterial infection may be obtained from the subject in need of treatment. The sample for testing may be from the site of the infection. A sample for testing may be obtained from the subject by swabbing of the skin, throat, or nose. A sample for testing may be obtained from the subject by collecting pus or fluids from wounds, abscesses, or other skin infections. A sample for testing may be obtained from the subject by collecting body fluids. The body fluids may include blood, sputum, urine, and/or other body fluids. Multiple samples may be taken from the subject. Multiple samples may be taken around the site of a prosthesis or medical device.

i. *Clostridium difficile*

The disclosed immunogenic proteins and compositions may be used to treat a *Clostridium difficile* infection. The disclosed immunogenic proteins and compositions may be administered to a subject who is at risk of developing a *Clostridium difficile* infection or is already diagnosed with a *Clostridium difficile* infection.

*Clostridium difficile* are anaerobic, motile bacteria, ubiquitous in nature, and especially prevalent in soil. *Clostridium difficile* infection cells are Gram-positive and show optimum growth on blood agar at human body temperatures in the absence of oxygen. When stressed, the bacteria may produce spores. The *Clostridium difficile* infection spores may be able to tolerate extreme conditions that the active bacteria cannot tolerate. Pathogenic *Clostridium difficile* infection strains produce multiple toxins. *Clostridium difficile* produces toxins. Two *Clostridium difficile* infection toxins are enterotoxin (*Clostridium difficile* toxin A (TcdA)) and cytotoxin (*Clostridium difficile* toxin B (TcdB)). Toxins A and B are glucosyltransferases that target and inactivate the Rho family of GTPases. TcdB may induce actin depolymerization by a mechanism correlated with a decrease in the ADP-ribosylation of the low molecular mass GTP-binding Rho proteins.

*Clostridium difficile* may be transmitted from person to person by the fecal-oral route. *Clostridium difficile* may be shed in feces. Any surface, device, or material (e.g., toilets, bathing tubs, and electronic rectal thermometers) that becomes contaminated with feces may serve as a reservoir for the *Clostridium difficile* spores. *Clostridium difficile* spores may be transferred to subjects via the hands of healthcare personnel who have touched a contaminated surface or item. *Clostridium difficile* may live for long periods of time on surfaces. *Clostridium difficile* spores may be heat-resistant. *Clostridium difficile* may not be not killed by alcohol-based hand cleansers or routine surface cleaning. *Clostridium difficile* spores may survive in clinical environments for long periods. Once spores are ingested, their acid-resistance may allow them to pass through the stomach unscathed. The *Clostridium difficile* spores may germinate and multiply into vegetative cells in the colon upon exposure to bile acids.

Antibiotic therapy for various infections may have the adverse effect of disrupting the normal balance of the gut flora. *Clostridium difficile* may grow in the presence of an antibiotic. *Clostridium difficile* may grow in the absence of other bacteria. The growth of *Clostridium difficile* may cause a *Clostridium difficile* infection in a subject.

Symptoms of a *Clostridium difficile* infection may include, but are not limited to watery diarrhea, fever, loss of appetite, nausea, abdominal pain/tenderness. Conditions that may result from a *Clostridium difficile* infection may include, but are not limited to pseudomembranous colitis (PMC), toxic megacolon, perforations of the colon, sepsis. A *Clostridium difficile* infection may be deadly. Administration of the disclosed immunogenic proteins or compositions may improve or prevent any one or more symptoms of *Clostridium difficile* infection.

b. Immunization

Administration of the disclosed immunogenic proteins and compositions comprising the same may immunize the subject against an infection. Immunization may fortify a subject's immune system against an immunogen. A subject may have an immune response in reaction to the presence of an immunogen after immunization with that immunogen. After immunization, the subject may develop the ability to quickly respond to a subsequent encounter with an immunogen because of immunological memory. This may be a function of the adaptive immune system. Therefore, by exposing a subject to an immunogen in a controlled way, the subject's body may protect itself in the presence of an immunogen.

The immunogen may be a *Clostridium difficile* immunogen. Immunizing a subject with a *Clostridium difficile* immunogen disclosed herein may prepare the subject's immune system to respond to *Clostridium difficile*. Immunizing a subject with a *Clostridium difficile* immunogen may prevent a *Clostridium difficile* infection. Immunizing a subject with a *Clostridium difficile* immunogen may treat a *Clostridium difficile* infection. The *Clostridium difficile* immunogen may be an immunogen disclosed herein. The *Clostridium difficile* immunogen may be Tcd169. The *Clostridium difficile* immunogen may be Tcd169Fl. The *Clostridium difficile* immunogen may be Tcd138Fl. *Clostridium difficile* colonization may be targeted. *Clostridium difficile* growth factors may be targeted. *Clostridium difficile* toxins may be targeted.

b. Modes of Administration

The disclosed immunogenic proteins or compositions may be administered to the subject by any suitable route. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the agent may be admixed with commonly known and used adjuvants and excipients such as for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire®).

For example, the route of administration may include, but is not limited to nasal mucosal, sublingual, oral, subcutaneous, intramuscular, intradermal, or intranasal.

A nasal mucosal route of administration may induce an immune response resulting in systemic and/or mucosal antibody response in a subject. The nasal mucosal route of administration may induce an immune response resulting in intestinal antibody response in a subject. The nasal mucosal route of administration may avoid protein digestion and degradation in the gastrointestinal tract. The nasal mucosal route of administration may require fewer antigens to be delivered than the oral route.

A sublingual route of administration may be used to deliver the disclosed immunogenic proteins and compositions to the bloodstream. The sublingual route of immunization may be easy to deliver. The sublingual route may have the potential for inducing broad systemic and mucosal immune response. The sublingual route of administration may induce intestinal mucosal immunity against infection with enteric pathogens. The sublingual mucosa may encompass the ventral side of the tongue and the floor of the mouth.

Oral administration may be the most effective method of protecting the gut against infection. Oral administration may expose the composition to proteolytic or hydrolyzing digestive enzymes, bile salts, extreme pH, rapid movement of contents, and limited access to the mucosal wall.

The disclosed immunogenic proteins and compositions may be administered to the subject parenterally. For parenteral administration, the immunogenic protein can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally, for parenteral administration, the immunogenic protein or composition can be in the form of an aqueous, lipid, oily or other kind of solution or suspension or even administered in the form of liposomes or nano-suspensions.

c. Combination Therapies

Additional therapeutic agent(s) may be administered simultaneously or sequentially with the disclosed immunogenic proteins and compositions. Sequential administration includes administration before or after the disclosed immunogenic proteins and compositions. In some embodiments, the additional therapeutic agent or agents may be administered in the same composition as the disclosed immunogenic proteins or compositions. In other embodiments, there may be an interval of time between administration of the additional therapeutic agent and the disclosed immunogenic proteins and compositions. In some embodiments, administration of an additional therapeutic agent with a disclosed immunogenic proteins and compositions may allow lower doses of the other therapeutic agents and administration at less frequent intervals. When used in combination with one or more other active ingredients, the immunogenic proteins and compositions of the present invention and the other active ingredients may be used in lower doses than when each is used singly. Accordingly, the immunogenic proteins and compositions of the present invention include those that contain one or more other active ingredients, in addition to immunogenic proteins and compositions. The above combinations include combinations of immunogenic proteins and compositions of the present invention not only with one other active compound, but also with two or more other active compounds.

d. Evaluation of Treatment

The efficacy of the methods of treatment with immunogenic proteins and compositions disclosed herein may be measured. The status of the bacterial infection may be monitored. The efficacy of the methods of treatment disclosed herein may be evaluated by the same or similar methods as used for diagnosis of the bacterial infection.

Evaluating the efficacy of the methods of treatment with the immunogenic proteins, and compositions disclosed herein or monitoring the bacterial infection may include, but are not limited to, symptomatic diagnostics, microbial culture, microscopy, biochemical tests, PCR based tests, and metagenomics sequencing. A microbial examination may include sample collection, microbial cultivation, identification, and test of antibiotic susceptibility. The evaluation or monitoring may include gram staining of the bacterial culture. The evaluation or monitoring may include a coagulase test of the bacterial culture. The evaluation or monitoring may include a catalase test of the bacterial culture. The evaluation or monitoring may include blood tests. The blood tests may include, but are not limited to, a full blood count, measurement of C-reactive protein, measurement of procalcitonin, and measurement of rapid plasma reagin. The evaluation or monitoring may include ELISA. The evaluation or monitoring may include PCR. The sample may be grown on an agar plate. The sample may be grown in nutrient broth. The growth conditions may include varying factors (e.g., type of growth medium, nutrients, selective compounds, antibiotics, temperature, pH level, oxygen level) to determine the type of bacteria growing. The presence, decreased presence, or lack of bacteria growing on an agar plate or in a nutrient broth may determine that the bacterial infection is improving or has been eradicated.

Samples for determining the efficacy of the methods of treatment with the immunogenic proteins, and compositions disclosed herein or monitoring the bacterial infection, may be obtained from the subject. The sample for testing may be from the site of the infection, or the site where the infection was previously present. A sample for testing may be obtained from the subject by swabbing of the skin, throat, or nose. A sample for testing may be obtained from the subject by collecting pus or fluids from wounds, abscesses, or other skin infections. A sample for testing may be obtained from the subject by collecting body fluids. The body fluids may include blood, sputum, urine, and other body fluids. Multiple samples may be taken from the subject. Multiple samples may be taken around the site of a prosthesis or medical device.

The evaluation of the efficacy of methods of treatment with the immunogenic proteins and compositions disclosed herein or monitoring of the bacterial infection may indicate that the subject requires continued treatment with the immunogenic proteins, and compositions disclosed herein. The evaluation of the efficacy of methods of treatment with immunogenic proteins and compositions disclosed herein or monitoring of the bacterial infection may indicate the eradication of the bacterial infection in the subject. The eradication of the bacterial infection may indicate that the subject no longer requires treatment with the immunogenic proteins and compositions disclosed herein.

5. KITS

The immunogenic proteins and compositions may be included in kits comprising the immunogenic proteins and compositions and information, instructions, or both that use of the kit will provide treatment for medical conditions in mammals (particularly humans). The kit may include an additional pharmaceutical composition for use in combination therapy. The kit may include buffers, reagents, or other components to facilitate the mode of administration. The kit may include materials to facilitate nasal mucosal administration. The kit may include materials that facilitate sublingual administration. The information and instructions may be in the form of words, pictures, or both, and the like. In addition or in the alternative, the kit may include the medicament, a composition, or both; and information, instructions, or both, regarding methods of application of medicament, or of composition, preferably with the benefit of treating or preventing medical conditions in mammals (e.g., humans).

The immunogenic proteins and compositions of the invention will be better understood by reference to the following examples, which are intended as an illustration of and not a limitation upon the scope of the invention.

6. EXAMPLES

Example 1. Construction of Recombinant Fusion Proteins

Figures 1A, 1B, 1C, 1D:
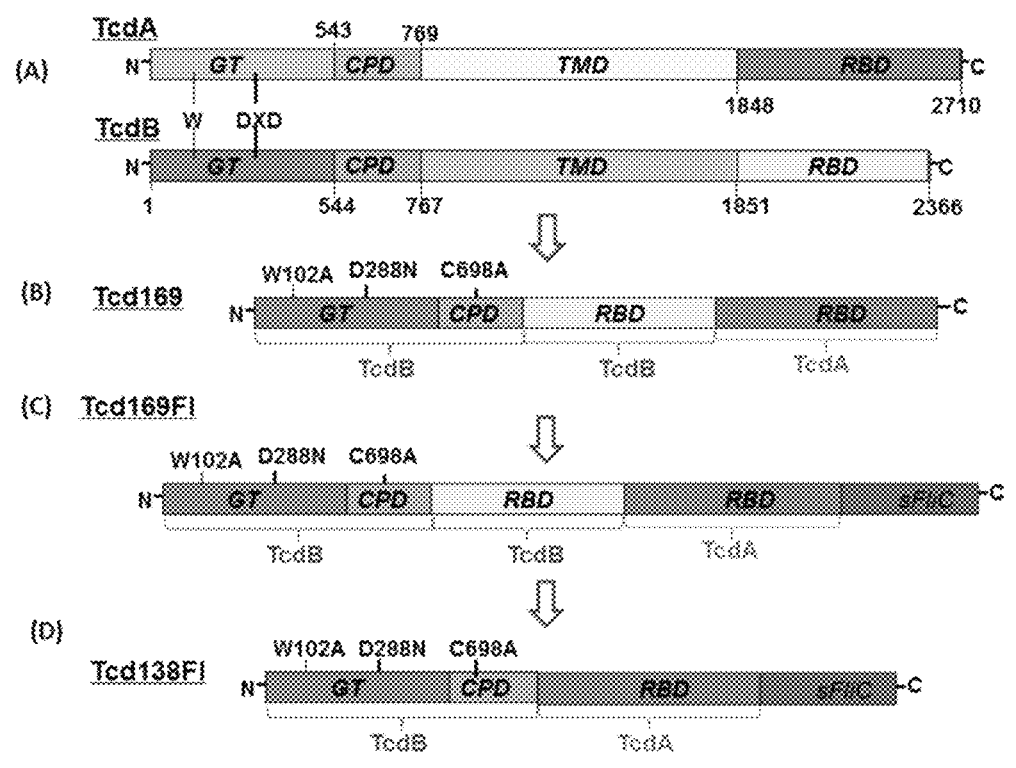

As shown in FIG. 1A, TcdA and TcdB share similar domains, including the glucosyltransferase domain (GT), the cysteine proteinase domain (CPD), the transmembrane domain (TMD) and the receptor binding domain (RBD). The DXD motif and a conserved tryptophan in the GT are involved in the enzymatic activity. FIG. 1B shows the construction of Tcd169. Tcd169 was constructed by fusing the GT, CPD, and RBD of TcdB with the RBD of TcdA. The GT and CPD of TcdB are connected without a GGSG linker. The CPD of TcdB is connected to the RBD of TcdB by a GGSG linker (SEQ ID NO: 1), and the RBD of TcdB is connected to the TBD of TcdA by a GGSG linker (SEQ ID NO: 1). Tcd169 lacks a transmembrane domain. Two point mutations, W102A and D288N, were made in the GT of TcdB, and a C689A point mutation was made in the CPD of TcdB. FIG. 1C shows the construction of Tcd169Fl. Tcd169Fl was made by fusing sFliC to Tcd169 with a GGSG linker (SEQ ID NO:1). As such, Tcd169Fl also lacks a transmembrane domain. FIG. 1D shows the construction of Tcd138Fl. Tcd138Fl was made by fusing the GT and CPD of TcdB with the RBD of TcdA, and fusing the RBD of TcdA to sFliC. The GT and CPD of TcdB are connected without a GGSG linker. The CPD of TcdB is connected to the RBC of TcdA by a GGSG linker (SEQ ID NO: 1), and the RBD of TcdA is connected to sFliC by a GGSG linker (SEQ ID NO: 1). Tcd138Fl lacks a transmembrane domain. Two point mutations, W102A and D288N, were made in the GT of TcdB, and a C698A point mutation was made in the CPD of TcdB.

Figure 3:
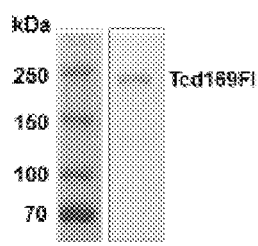
FIG. 3 shows the expression and purification of Tcd169Fl.

The chimeric DNA encoding the recombinant proteins was ligated into *B. megaterium* expression vector which adds a C-terminal His-tag to the chimeric proteins. The proteins were subsequently purified from bacterial lysate by Ni-affinity chromatography and gel filtration, and analyzed by SDS-PAGE. FIG. 2 and FIG. 3 show expression and purification of Tcd169 and Tcd169Fl, respectively.

Example 2. Expression of *Clostridium difficile* Protein Cwp84

Figure 4:
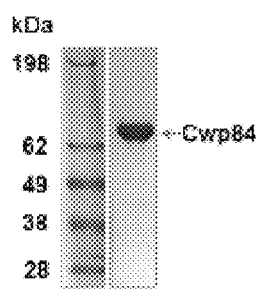
FIG. 4 shows the expression and purification of *Clostridium difficile* Cwp84 protein.

To include Cwp84 as a component targeting *Clostridium difficile* colonization, Cwp84 was expressed and purified using an *E. coli* expression system. Gene sequence coding for *Clostridium difficile* Cwp84 was synthesized and cloned into pET21b(+) in *E. coli* BL21(DE3). Cwp84 protein was purified from bacterial lysate by Ni-affinity chromatography and an ion-exchange fractionation, and analyzed by SDS-PAGE. FIG. 4 shows expression and purification of Cwp84.

Figure 5:
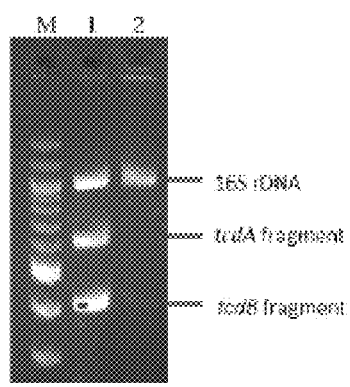
FIG. 5 shows the toxin gene profiles of two selected *Clostridium difficile* strains. Lane 1, tcdA$^+$, tcdB$^+$; Lane 2, non-toxigenic *C. difficile*; Lane M: 100-bp DNA marker. A rapid 3-plex PCR was developed for the detection of tcdA, tcdB and 16s rDNA. 5 µl of 12-24 hrs of *Clostridium difficile* culture was used as template.

Example 3. Rapid Identification of Toxigenic/Non-Toxigenic *Clostridium difficile* Strains by Multiplex PCR To rapidly identify toxigenic/non-toxigenic *Clostridium difficile* strains, a simple and fast 3-plex PCR method was developed to identify tcdA, tcdB and 16s rDNA specific for *Clostridium difficile*. In this method, 5 μl of 12-24 hrs of *Clostridium difficile* culture was used as template (FIG. 5). This method will be used to distinguish toxigenic *Clostridium difficile* strains from non-toxigenic *Clostridium difficile* strains.

Figure 6:
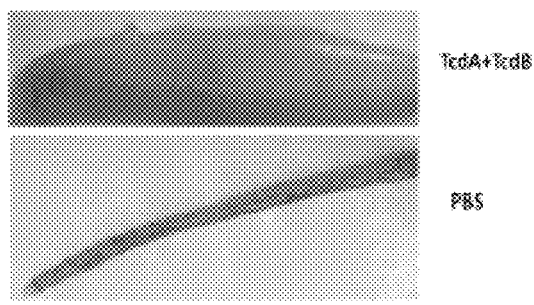
FIG. 6 shows the colonic inflammation and injury caused by direct intra-rectal instillation of TcdA/TcdB. A 5F infant feeding tube was inserted 2.5 cm up the colon. 100 µl of TcdA (10 µg)+TcdB (10 µg) or PBS was slowly administered. 4 or 5 hours later mice were euthanized and dissected to analyze the toxin-mediated effects on the colon.

Example 4. Establishment of Novel and More Efficient Mouse Model of *Clostridium difficile* Toxin Exposure A mouse model of *Clostridium difficile* toxin exposure was developed. A 5F infant feeding tube catheter with side ports (Mallinckrodt Inc., St. Louis, Mo.; catalogue no. 85771) was inserted 2.5 cm up the colon. At this point, 100 μl of TcdA (10 μg)+TcdB (10 μg) or PBS was slowly administered over 30 seconds while pressure was applied to the anal area to prevent leakage. Following injection of the solution, the tube was slowly removed and the rectal pressure was maintained for a further 30 seconds. Four hours later, mice were euthanized and dissected to analyze the toxin-mediated effects on the colon. The administration of TcdA/TcdB triggered dramatic colonic inflammation (FIG. 6) and neutrophil and macrophage infiltration. This "intra-rectal toxin instillation" approach may be used to determine immunization protection against toxin challenge via rectum.

Figures 8A, 8B, 8C, 8D, 8E:
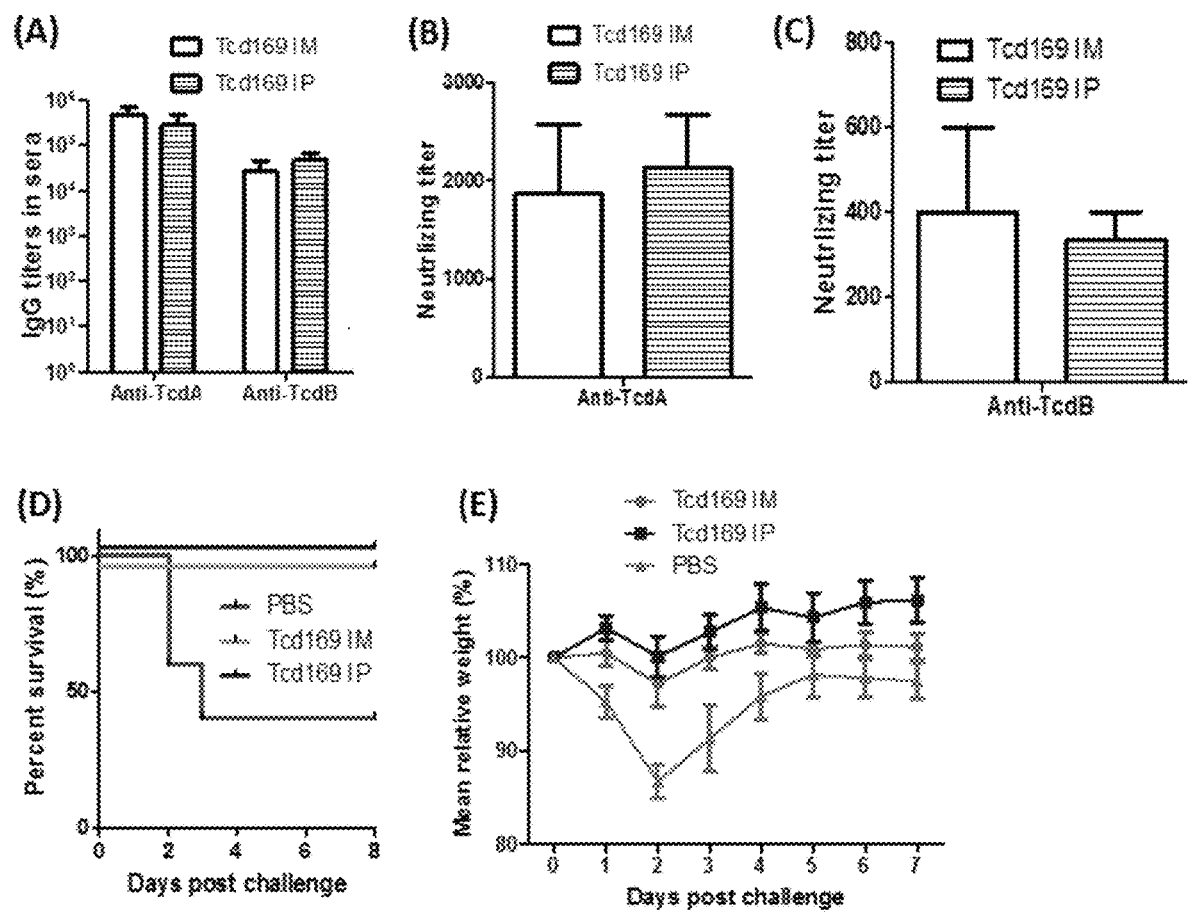
FIGS. 8A-8E show the protective responses of Tcd169 immunization (IM or IP) in mice. Groups of C57 BL/6 mice (n=10) were immunized with Tcd169 (10 µg) or PBS in the presence of alum for 3 times at 14-day intervals (IM or IP). Anti-toxin IgG titers (FIG. 8A) and anti-toxin neutralizing titers (FIG. 8B, FIG. 8C) in sera from third immunization were measured. Seven days after third immunization, mice were given antibiotic mixture in drinking water for 4 days, switched to regular water for 2 days, and were given one dose of clindamycin (10 mg/kg) one day before infection with $10^6$ of *Clostridium difficile* UK6 spores by gavage. After infection, mouse survivals (P=0.0486 between PBS and Tcd169 IM/Tcd169 IP groups) (FIG. 9D), and mean relative weight changes (FIG. 8E) of different groups were recorded. The neutralizing titer is expressed as the maximum dilution of the sera that inhibits Vero cell rounding caused by toxin at a given concentration. This given concentration is the minimum toxin dose causing cell rounding after a 16 h of toxin exposure, i.e., 2.5 and 0.1 ng/ml for TcdA and TcdB, respectively.

Example 5. Tcd169 Immunization Induces Protective Responses Against Both Toxins and Infection with an Epidemic *Clostridium difficile* Strain Groups of C57 BL/6 mice (n=10) were immunized with Tcd169 (10 μg) or PBS in the presence of alum for 3 times at 14-day intervals (IM or IP). Immunization with Tcd169 via intraperitoneal (i.p), intramuscular (i.m.) routes induced similar levels of IgG antibody responses against both toxins (FIG. 8A). Tcd169 immunization induced potent neutralizing antibodies against both toxins (FIG. 8B and FIG. 8C). Protection efficacy of Tcd169 immunization was evaluated in a mouse model of CDI. After three immunizations (10 μg Tcd169 per immunization with Alum as adjuvant, at 14-day intervals) via i.p. or i.m. route, mice were challenged with $10^6$ spores of *Clostridium difficile* UK6 (BI/NAP1/027). In vehicle-immunized mice, significant disease symptoms including weight loss (FIG. 8E) and severe diarrhea in all mice. Approximately 40% of mice succumbed by day 3 (FIG. 8D). In contrast, all Tcd169-immunized mice survived (FIG. 8D) and showed no signs of weight loss (FIG. 8E).

Figures 9A, 9B, 9C, 9D, 9E, 9F:
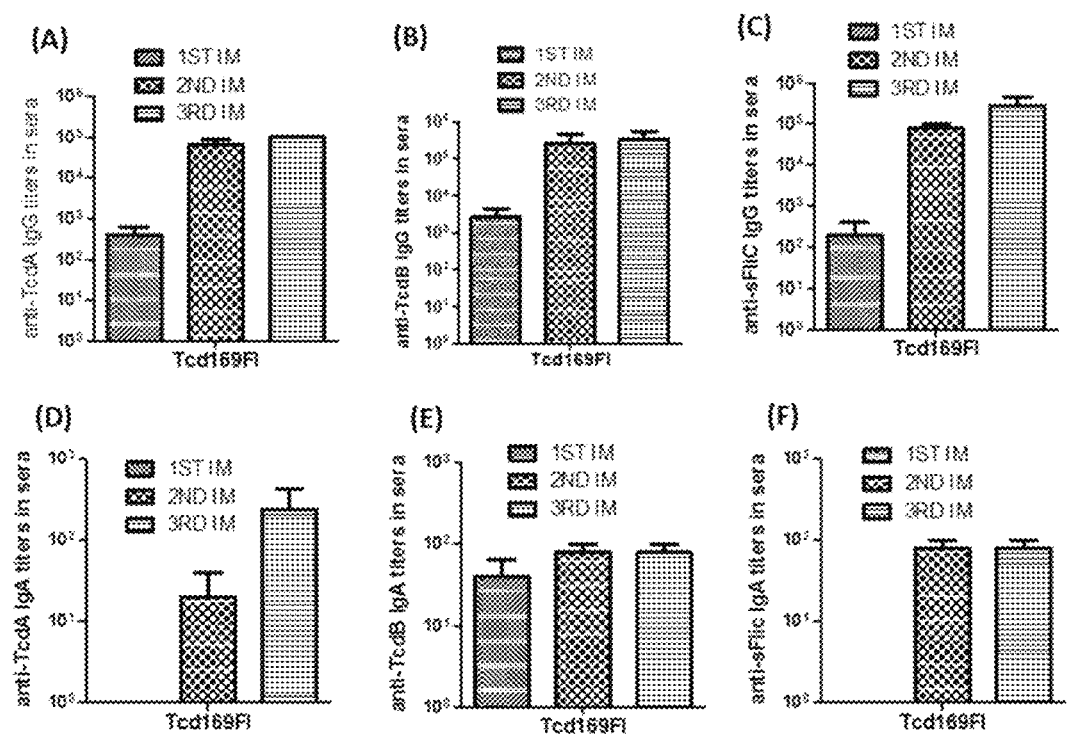
FIGS. 9A-9F show that intramuscular immunization of mice with Tcd169Fl induces potent anti-toxin/sFliC responses. Groups of C57 BL/6 mice (n=10) were immunized with Tcd169Fl (10 µg) or PBS in the presence of alum for 3 times at 14-day intervals (IM). IgG titers against TcdA (FIG. 9A), TcdB (FIG. 9B), or sFliC (FIG. 9C), and IgA titers against TcdA (FIG. 9D), TcdB (FIG. 9E), or sFliC (FIG. 9F) were determined.

FIG. 9 shows that intramuscular immunization of mice with Tcd169Fl induces potent anti-toxin/sFliC responses. Groups of C57 BL/6 mice (n=10) were immunized with Tcd169Fl (10 μg) or PBS in the presence of alum for 3 times at 14-day intervals (IM). IgG titers against TcdA (FIG. 9A), TcdB (FIG. 9B), or sFliC (FIG. 9C), and IgA titers against TcdA (FIG. 9D), TcdB (FIG. 9E), or sFliC (FIG. 9F) were determined.

Figures 10A, 10B, 10C:
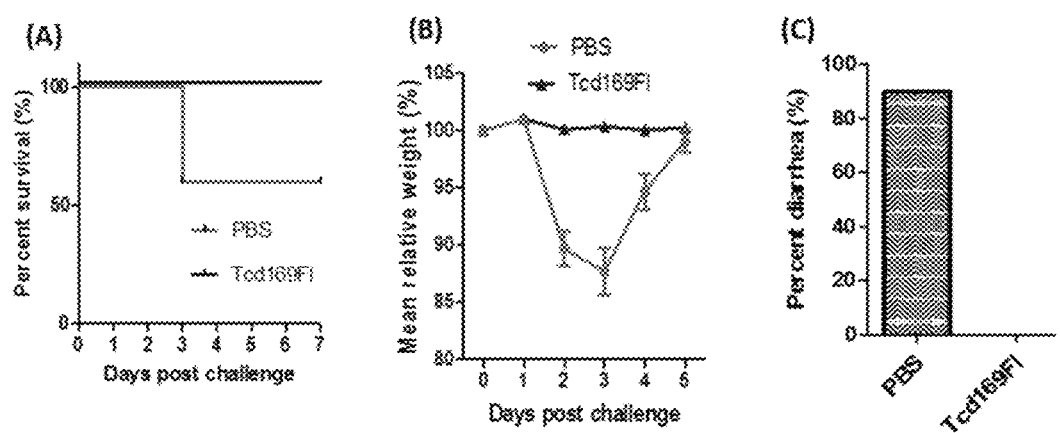
FIGS. 10A-10C show that immunization with Tcd169Fl provides mice full protection against infection with hypervirulent *Clostridium difficile* UK1. Seven days after third immunization with Tcd169Fl, mice were given antibiotic mixture in drinking water for 4 days, switched to regular water for 2 days, and were given one dose of clindamycin (10 mg/kg) one day before infection with $10^6$ of *Clostridium difficile* UK1 spores by gavage. After infection, mouse survivals (P=0.0486 between PBS and Tcd169Fl) (FIG. 10A), mean relative weight changes (FIG. 10B) and percent diarrhea (FIG. 10C) of different groups were recorded.

FIG. 10 shows that immunization with Tcd169Fl provides mice full protection against infection with hypervirulent *Clostridium difficile* UK1. Seven days after third immunization with Tcd169Fl, mice were given antibiotic mixture in drinking water for 4 days, switched to regular water for 2 days, and were given one dose of clindamycin (10 mg/kg) one day before infection with $10^6$ of *Clostridium difficile* UK1 spores by gavage. After infection, mouse survivals (P=0.0486 between PBS and Tcd169Fl) (FIG. 10A), mean relative weight changes (FIG. 10B) and percent diarrhea (FIG. 10C) of different groups were recorded.

Example 6. Determine Antibody Responses and Protection Against Systemic Toxin Challenge in Mice Immunized Intramuscularly with Tcd169Fl or Tcd169Fl and Cwp84 ("Tcd169Fl/Cw")

Groups of C57BL/6 mice (n=10) aged 6 weeks may be immunized IM with 10 μg of Tcd169Fl or Tcd169Fl and Cwp84 ("Tcd169Fl/Cw") (10 μg each). Alum may be used as adjuvant for IM immunization. Sera and feces may be collected after each immunization and the anti-toxin, anti-sFliC or anti-Cwp IgA and IgG measured by ELISA.

Example 7. Determine Protection Against Systemic Toxin Challenge

A potent antibody response may be generated, that protects mice against challenge with a lethal dose of TcdA/TcdB (100 ng for each toxin). One week after the third immunization, mice may be challenged IP with a lethal dose of TcdA, TcdB or a mixture of TcdA and TcdB (100 ng for each toxin), and monitored for 72 hrs. If the protection is not optimal, dose optimization experiments may be performed.

Example 8. Optimize Immunization Dose

The initial experiment may use 10 μg of Tcd169Fl and Tcd169Fl/Cw (10 μg each, IM). Dose optimization of the immunogens may follow by doubling and halving the initial immunization dose, and the lowest amount of antigen required to induce the highest level of serum/fecal antibody response for each immunogen may be established.

Example 9. 1d. Challenge the Immunized Mice with Wild-Type Toxins to Determine $LD_{50}$im (Lethal Dose, 50% Death) for Each Toxin and for the Combination of the Two One week after the third immunization with optimal dose of Tcd169Fl or Tcd169Fl/Cw, mice may be challenged with doubling doses of 100 ng of TcdA/TcdB or the combination of two. The lethal dose for TcdA/TcdB in mice with body weight around 16-20 g is 100 ng. The dose that causes death of 50% of immunized mice may be determined, and designated as $LD_{50}$im. The $LD_{50}$im of each toxin for each immunogen may be determined.

Example 10. Determine the In Vitro Antibody Neutralizing Titers Against Each Toxin, and Determine Anti-Adherence Capability of Antibody Against Adhesion of *Clostridium Difficile* to Intestinal Epithelial Cells One week after the third immunization with optimal dose of Tcd169Fl or Tcd169Fl/Cw, sera and feces from each immunized mouse may be collected. Sera or feces from each group may be pooled together. Feces may be dissolved (0.1 g/ml) in PBS containing proteinase inhibitors. Abilities of sera and feces to neutralize the cytotoxicity of TcdA or TcdB may be measured.

The adherence of the *Clostridium difficile* strains to human colonic enterocyte-like Caco-2 cells may be used to assess in vitro anti-adherence capability of sera and feces. Caco-2 cells in 24-well plates in DMEM may be incubated at 37° C. in 5% $CO_2$ incubator for 15 days with daily medium change. Overnight *Clostridium difficile* cultures may be pelleted, washed and resuspended in DMEM, adjusted to $10^8$ cfu/ml. 100 ul of sera or fecal samples (dissolved in PBS) may be added per well, and plates incubated for 1 h. Bacterial suspension (0.5 ml) may then be added to each well (with or without antibody) and plates may then be incubated for 1.5 h at 37° C. under anaerobic conditions. The non-adherent bacteria may be removed by washing five times with PBS and the bound bacteria may be detached by adding 0.5 ml 1% saponin per well. Serial dilutions may be plated on BHI agar plates and colonies may be counted after 48 h of incubation. In parallel, uninfected monolayers (negative control) may be collected by trypsinization, and counted by trypan blue staining in order to express the adherence results as number of viable adherent cfu per one Caco-2 cell. Each adherence assay may be performed in triplicate, and repeated three times.

Example 11. Immunization of Mice

Groups of mice immunized with immunogens 1) lacking adjuvant, or including 2) dmLT or CpG ODNs may be compared. CpG ODNs may be purchased from Invivogen.

The outcome of immunization of each immunogen mixed with 5 μg or 10 μg of dmLT or CpG ODNs for IN, SL, and oral immunizations may be compared. Groups of mice may be immunized three times with Tcd169Fl or Tcd169Fl/Cw intranasally (IN), sublingually (SL), or orally. Serum and fecal antibody responses may be measured after each immunization.

Example 12. Routes of Immunization

For Intranasal immunization (IN), 5 μl of Tcd169Fl or Tcd169Fl/Cw with or without adjuvant may be delivered into each nostril (total 10 μl per mouse). The volume of 5 μl per nostril may ensure that all immunogens may be distributed inside of nasal cavity.

For sublingual (SL) immunization, mice may be anesthetized with ketamine/xylazine, and 5 μl of Tcd169Fl or Tcd169Fl/Cw, with or without adjuvant may be delivered at the ventral side of the tongue and directed toward the floor of the mouth.

Figures 7A, 7B:
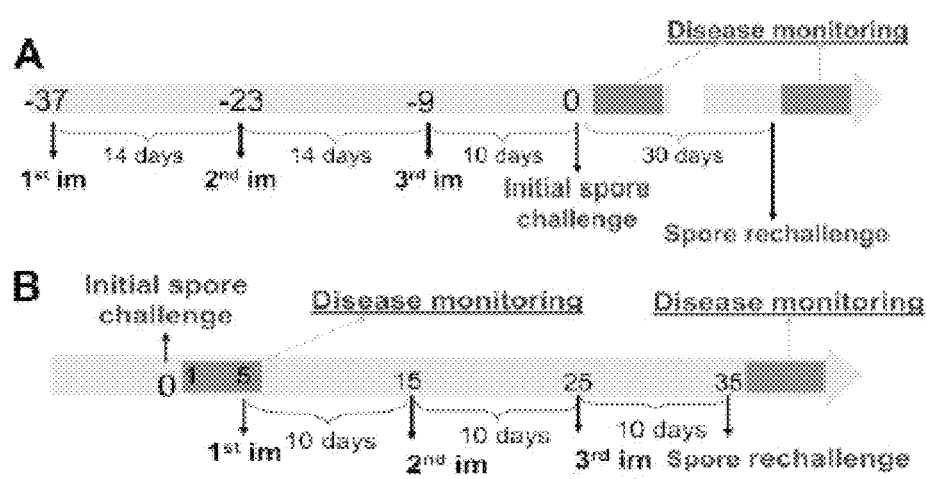
FIGS. 7A-7B show immunization and challenge schemes for CDI relapse models in mice. After 3 immunizations mice may be pretreated with antibiotic mixture, challenged with *Clostridium difficile* UK6 spores, and monitored for about a week. Thirty days after initial spore challenge, survived mice may be again treated with antibiotics mixture followed by infection with *Clostridium difficile* UK6 spores and monitoring (FIG. 7A). Non-immunized naïve mice may be pretreated with antibiotic mixture, challenged with *Clostridium difficile* UK6 spores, and monitored for about a week. Starting on post-infection day 5, mice may be immunized for 3 times at 10-day intervals. Ten days after third immunization, mice may be again treated with antibiotics mixture followed by infection with *Clostridium difficile* UK6 spores and monitoring (FIG. 7B).

Example 13. In Vitro Neutralization Titers for Both Systemic and Mucosal Antibodies, and Anti-Adherence Capability of Antibody Against Adhesion of *Clostridium difficile* to Intestinal Epithelial Cells The neutralizing titers against TcdA and TcdB, and anti-adherence capability of sera and mucosal samples against adhesion of *Clostridium difficile* to intestinal epithelial cells may be determined.

Example 14. Protection Against Systemic Challenge of the Toxins

Protection against systemic toxin challenge may be performed. $LD_{50}$im may be used as the standard challenge dose to assess the levels of the protection against systemic toxin challenge induced by the mucosal immunization for each immunogen. The mucosal immunizations may induce a similar level of protection as do parenteral immunization, in which 50% of mice may survive from challenge with $LD_{50}$im dose of each wild type toxin, or two toxins given together. Should greater than 50% of mice die, a dose optimization may be performed as described below.

Example 15. Protection Against Mucosal Challenge with Toxins

In the above experiments, the generation of mucosal IgA and IgG antibodies against toxins may be examined. It may be assessed whether these antibodies produced in the gut can protect mice against toxin-mediated destruction of the mucosa. The "intra-rectal toxin instillation" approach may be used.

One week after the third immunization, mice (immunized with immunogens or placebo) may be directly injected with 10 μg of TcdA or TcdB or both (10 μg each) in a volume of 100 μl via rectum. Four hours later, mice may be euthanized and the colon may be carefully removed. Toxin-induced fluid accumulation may be quantitated as the ratio of weight to length. In addition to assessing the fluid accumulation, the pathological signs, such as neutrophil infiltration and villus damage, may be evaluated histologically. Histopathological and neutrophil myeloperoxidase (MPO) activity assays may be performed to evaluate mucosal damage and neutrophil infiltration. The resected colons may be fixed in 4% formaldehyde buffered with PBS and then embedded with paraffin. Deparaffinized 6-μm-thick sections may be stained with haematoxylin and eosin (H&E) for histological analysis, and the tissue injuries may be blindly scored by a histologist. Histological grading criteria may be as follows: 0, minimal infiltration of lymphocytes, plasma cells, and eosinophils; 1+, mild infiltration of lymphocytes, plasma cells, neutrophils, and eosinophils plus mild congestion of the mucosa with or without hyperplasia of gut-associated lymphoid tissue; 2+, moderate infiltrations of mixed inflammatory cells, moderate congestion and edema of the lamina propria, with or without goblet cell hyperplasia, individual surface cell necrosis or vacuolization, and crypt dilatation; 3+, severe inflammation, congestion, edema, and hemorrhage in the mucosa, surface cell necrosis, or degeneration with erosions or ulcers. To measure MPO activities, a portion of the resected colon may be homogenized in 1 ml of 50 mM potassium phosphate buffer with 0.5% hexadecyl trimethyl ammonium bromide and 5 mM EDTA. MPO activities in a centrifuged supernatant may be determined using a substrate o-phenylenediamine in a solution containing 0.05% of H2O2 followed by measuring absorbance at 490 nm.

Example 16. Dose Optimization

Dose optimization of antigens may follow by performing doubling and halving the optimized doses determined in previous examples for 4 immunogens. If an adjuvant is used, e.g. dmLT, the same amount of the adjuvant may be mixed together with the immunogen before injection. For each dose and route of immunization, both systemic and mucosal IgG and IgA response may be monitored and their neutralizing titers may be measured. The lowest amount of antigen required to induce the highest level of serum and mucosal antibody response for each immunogen may be established.

Example 17. Evaluate the Efficacy of the Top-Ranked Regimen of Systemic and Mucosal Immunizations Respectively for Tcd169Fl and Tcd169Fl/Cw in Protecting Mice Against Primary and Recurrent CDI After 3 immunizations, mice may be pretreated with an antibiotic mixture in drinking water prior to oral challenge with $10^6$ *Clostridium difficile* UK6 spores. After infection, mice may be monitored for weight loss, diarrhea and modality. Feces may be collected from the day of spore challenge until day 7 post-challenge for counting *Clostridium difficile* spores and measuring toxin levels. During the period of antibiotic pretreatment, *Clostridium difficile* challenge and post-infection, mice may be maintained in sterile cages and given sterilized food and water. Cages, food and water may be changed daily until the end of experiments.

For enumeration of *Clostridium difficile* spore secretion in feces, fecal samples collected from the day of spore challenge until day 7 post-challenge (from both immunized and non-immunized control groups) may be dissolved (0.1 g/ml) in PBS containing proteinase inhibitors, serially diluted to count *Clostridium difficile* spores. Toxin levels in fecal samples may be determined by ELISA.

Example 18. Protection Against Recurrent CDI in Mice

CDI has become increasingly difficult to manage due, in part, to the ineffectiveness of current antibiotic regimens which are associated with high relapse rates. The efficacy of top-ranked regimens of immunization in preventing disease recurrence in a spore-induced mouse CDI recurrence model which was developed previously may be evaluated. To induce CDI relapse, surviving mice may be given antibiotic cocktail treatment followed by oral gavage of *Clostridium difficile* UK6 spores ($10^6$/mouse) 30 days after the primary infection. The immunization and challenge scheme is illustrated in FIG. 7A. To assess whether immunization also protects against disease relapse in naïve animals that recovered from CDI, surviving mice may be immunized after their recovery from the initial CDI as illustrated (FIG. 8B).

Example 19. Evaluation of the Efficacy of the Top-Ranked Regimen of Systemic and/or Mucosal Immunizations Respectively for Tcd169Fl and Tcd169Fl/Cw, in a Hamster Model of CDI For IN immunization, 5 µl of Tcd169Fl or Tcd169Fl/Cw, with or without adjuvant may be delivered into each nostril (total 10 µl per mouse). The volume of 5 µl per nostril may ensure that all immunogens may be distributed inside of nasal cavity.

For SL immunization, hamsters may be anesthetized with ketamine/xylazine, and 10 µl of Tcd169Fl or Tcd169Fl/Cw, with or without adjuvant may be delivered at the ventral side of the tongue and directed toward the floor of the mouth.

For oral immunization, 200 µl-400 µl of immunogens may be given to hamsters by gavage.

Example 20. Protection Against CDI in Hamsters

After three immunizations, hamsters may be pretreated with clindamycin followed by challenged with 100 to $10^4$ *Clostridium difficile* UK6 spores. Weight changes, diarrhea, and modality may be recorded. After infection, fecal samples may be collected for 10 days to compare spore secretion and toxin levels in feces from immunized and non-immunized groups.

It is understood that the foregoing detailed description and accompanying examples are merely illustrative and are not to be taken as limitations upon the scope of the invention, which is defined solely by the appended claims and their equivalents.

Various changes and modifications to the disclosed embodiments may be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the present disclosure are set out in the following numbered clauses:

Clause 1: An immunogenic protein comprising:
 i) a glucosyltranferase domain of *Clostridium difficile* toxin TcdB;
 ii) a cysteine proteinase domain of *Clostridium difficile* toxin TcdB; and
 iii) a receptor binding domain of *Clostridium difficile* toxin TcdA, wherein the immunogenic protein lacks a transmembrane domain.

Clause 2: The immunogenic protein of clause 1, wherein the immunogenic protein further comprises a receptor binding domain of *Clostridium difficile* toxin TcdB.

Clause 3: The immunogenic protein of clause 1 or 2, wherein the immunogenic protein further comprises *Salmonella typhimurium* flagellin.

Clause 4: The immunogenic protein of any one of clauses 1-3, wherein the immunogenic protein further comprises a receptor binding domain of *Clostridium difficile* toxin TcdB and *Salmonella typhimurium* flagellin.

Clause 5: The immunogenic protein of any one of clauses 1-4, wherein the glucosyltransferase domain of *Clostridium difficile* toxin TcdB comprises a W102A amino acid substitution and a D288N amino acid substitution.

Clause 6: The immunogenic protein of any one of clauses 1-5, wherein the cysteine proteinase domain of *Clostridium difficile* toxin TcdB comprises a C698A amino acid substitution.

Clause 7: A pharmaceutical composition comprising the immunogenic protein of any one of clauses 1-6 and a pharmaceutically acceptable carrier.

Clause 8: A method of treating a *Clostridium difficile* bacterial infection in a subject in need thereof, the method comprising administering to the subject the immunogenic protein of any one of clauses 1-6 or the pharmaceutical composition of clause 7.

Clause 9: An immunogenic protein comprising:
 i) a glucosyltransferase domain (GT) of *Clostridium difficile* toxin TcdB;
 ii) a cysteine proteinase domain (CPD) of *Clostridium difficile* toxin TcdB;
 iii) a receptor binding domain (RBD) of *Clostridium difficile* toxin TcdB; and
 iv) a receptor binding domain (RBD) of *Clostridium difficile* toxin TcdA;
 wherein the GT of *Clostridium difficile* toxin TcdB comprises a W102A amino acid substitution and a D288N amino acid substitution and the CPD of *Clostridium difficile* toxin TcdB comprises a C698A amino acid substitution, and wherein the immunogenic protein lacks a transmembrane domain.

Clause 10: The immunogenic protein of clause 9 wherein the immunogenic protein comprises the amino acid sequence of SEQ ID NO.: 5.

Clause 11: The immunogenic protein of clause 9 or 10, wherein the immunogenic protein further comprises flagellin of *Salmonella typhimurium* (sFliC).

Clause 12: The immunogenic protein of clause 11, wherein the immunogenic protein comprises the amino acid sequence of SEQ ID NO.: 6.

Clause 13: A pharmaceutical composition comprising the immunogenic protein of any one of clauses 9-12 and a pharmaceutically acceptable carrier.

Clause 14: A method of treating a *Clostridium difficile* bacterial infection in a subject in need thereof, the method comprising administering to the subject the immunogenic protein of any one of clauses 9-12 or the pharmaceutical composition of clause 13.

Clause 15: A pharmaceutical composition comprising the immunogenic protein of clause 11 and a *Clostridium difficile* Cwp84 protein.

Clause 16: A method of treating a *Clostridium difficile* bacterial infection in a subject in need thereof, the method comprising administering to the subject the pharmaceutical composition of clause 15.

Clause 17: An immunogenic protein comprising:
 i) a glucosyltransferase domain (GT) of *Clostridium difficile* toxin TcdB;
 ii) a cysteine proteinase domain (CPD) of *Clostridium difficile* toxin TcdB;
 iii) a receptor binding domain (RBD) of *Clostridium difficile* toxin TcdA; and
 iv) flagellin of *Salmonella typhimurium* (sFliC);

wherein the GT of *Clostridium difficile* toxin TcdB comprises a W102A amino acid substitution and a D288N amino acid substitution and the CPD of *Clostridium difficile* toxin TcdB comprises a C698A amino acid substitution, and wherein the immunogenic protein lacks a transmembrane domain.

Clause 18: The immunogenic protein of clause 17, wherein the immunogenic protein comprises the amino acid sequence of SEQ ID NO.: 7.

Clause 19: A pharmaceutical composition comprising the immunogenic protein of clause 17 or 18 and a pharmaceutically acceptable carrier.

Clause 20: A method of treating a *Clostridium difficile* bacterial infection in a subject in need thereof, the method comprising administering to the subject the immunogenic protein of clause 17 or 18 or the pharmaceutical composition of clause 19.

Clause 21: The pharmaceutical composition of any one of clauses 7, 13, or 19, wherein the composition further comprises one or more *Clostridium difficile* immunogens.

Clause 22: The pharmaceutical composition of clause 21, wherein the one or more *Clostridium difficile* immunogens is a Cwp84 protein.

Clause 24: A method of treating a *Clostridium difficile* bacterial infection in a subject in need thereof, the method comprising administering to the subject the pharmaceutical composition of any one of clauses 21-24.

What is claimed is:

1. A pharmaceutical composition comprising an immunogenic protein and a *Clostridium difficile* Cwp84 protein, wherein the immunogenic protein comprises:
   i) a glucosyltransferase domain (GT) of *Clostridium difficile* toxin TcdB;
   ii) a cysteine proteinase domain (CPD) of *Clostridium difficile* toxin TcdB;
   iii) a receptor binding domain (RBD) of *Clostridium difficile* toxin TcdB;
   iv) a receptor binding domain (RBD) of *Clostridium difficile* toxin TcdA; and
   v) flagellin of *Salmonella typhimurium* (sFliC);
   wherein the GT of *Clostridium difficile* toxin TcdB comprises a W102A amino acid substitution and a D288N amino acid substitution when compared to SEQ ID NO.: 8 and the CPD of *Clostridium difficile* toxin TcdB comprises a C698A amino acid substitution when compared to SEQ ID NO.: 8, and wherein the immunogenic protein lacks a transmembrane domain.

2. The pharmaceutical composition of claim 1, wherein the GT of *Clostridium difficile* toxin TcdB is positioned immediately upstream of the CPD of *Clostridium difficile* toxin TcdB, wherein the amino acid sequence of the linked GT of *Clostridium difficile* toxin TcdB and the CPD of *Clostridium difficile* toxin TcdB is set forth in SEQ ID NO.: 8; wherein the RBD of *Clostridium difficile* toxin TcdA comprises the amino acid sequence of SEQ ID NO.: 9; and wherein the RBD of *Clostridium difficile* toxin TcdB comprises the amino acid sequence of SEQ ID NO.: 10.

3. The pharmaceutical composition of claim 1, wherein the RBD of *Clostridium difficile* toxin TcdA is positioned immediately upstream of sFliC.

4. The pharmaceutical composition of claim 1, wherein the immunogenic protein comprises the amino acid sequence of SEQ ID NO.: 6.

5. The pharmaceutical composition of claim 1 further comprising a pharmaceutically acceptable carrier.

6. The pharmaceutical composition of claim 1 further comprising an adjuvant that is selected from the group consisting of alum, an unmethylated CpG motif, and dmLT.

7. A method of treating a *Clostridium difficile* bacterial infection in a subject in need thereof, the method comprising administering to the subject a therapeutically effective amount of a pharmaceutical composition that comprises an immunogenic protein and a *Clostridium difficile* Cwp84 protein, wherein the immunogenic protein comprises:
   i) a glucosyltransferase domain (GT) of *Clostridium difficile* toxin TcdB;
   ii) a cysteine proteinase domain (CPD) of *Clostridium difficile* toxin TcdB;
   iii) a receptor binding domain (RBD) of *Clostridium difficile* toxin TcdB;
   iv) a receptor binding domain (RBD) of *Clostridium difficile* toxin TcdA; and
   v) flagellin of *Salmonella typhimurium* (sFliC);
   wherein the GT of *Clostridium difficile* toxin TcdB comprises a W102A amino acid substitution and a D288N amino acid substitution when compared to SEQ ID NO.: 8 and the CPD of *Clostridium difficile* toxin TcdB comprises a C698A amino acid substitution when compared to SEQ ID NO.: 8, and wherein the immunogenic protein lacks a transmembrane domain.

8. The method of claim 7, wherein the GT of *Clostridium difficile* toxin TcdB is positioned immediately upstream of the CPD of *Clostridium difficile* toxin TcdB, wherein the amino acid sequence of the linked GT of *Clostridium difficile* toxin TcdB and the CPD of *Clostridium difficile* toxin TcdB is set forth in SEQ ID NO.: 8; wherein the RBD of *Clostridium difficile* toxin TcdA comprises the amino acid sequence of SEQ ID NO.: 9; and wherein the RBD of *Clostridium difficile* toxin TcdB comprises the amino acid sequence of SEQ ID NO.: 10.

9. The method of claim 7, wherein the RBD of *Clostridium difficile* toxin TcdA is positioned immediately upstream of sFliC.

10. The method of claim 7, wherein the immunogenic protein comprises the amino acid sequence of SEQ ID NO.: 6.

11. The method of claim 7 further comprising a pharmaceutically acceptable carrier.

12. The method of claim 7 further comprising an adjuvant that is selected from the group consisting of alum, an unmethylated CpG motif, and dmLT.

13. A method of treating pseudomembranous colitis or sepsis in a subject in need thereof, the method comprising administering to the subject a therapeutically effective amount of a pharmaceutical composition that comprises an immunogenic protein and a *Clostridium difficile* Cwp84 protein, wherein the immunogenic protein comprises:
   i) a glucosyltransferase domain (GT) of *Clostridium difficile* toxin TcdB;
   ii) a cysteine proteinase domain (CPD) of *Clostridium difficile* toxin TcdB;
   iii) a receptor binding domain (RBD) of *Clostridium difficile* toxin TcdB;
   iv) a receptor binding domain (RBD) of *Clostridium difficile* toxin TcdA; and
   v) flagellin of *Salmonella typhimurium* (sFliC);
   wherein the GT of *Clostridium difficile* toxin TcdB comprises a W102A amino acid substitution and a D288N amino acid substitution when compared to SEQ ID NO.: 8 and the CPD of *Clostridium difficile* toxin TcdB comprises a C698A amino acid substitution when compared to SEQ ID NO.: 8, and wherein the immunogenic protein lacks a transmembrane domain.

14. The method of claim 13, wherein the GT of *Clostridium difficile* toxin TcdB is positioned immediately upstream of the CPD of *Clostridium difficile* toxin TcdB, wherein the amino acid sequence of the linked GT of *Clostridium difficile* toxin TcdB and the CPD of *Clostridium difficile* toxin TcdB is set forth in SEQ ID NO.: 8; wherein the RBD of *Clostridium difficile* toxin TcdA comprises the amino acid sequence of SEQ ID NO.: 9; and wherein the RBD of *Clostridium difficile* toxin TcdB comprises the amino acid sequence of SEQ ID NO.: 10.

15. The method of claim 13, wherein the RBD of *Clostridium difficile* toxin TcdA is positioned immediately upstream of sFliC.

16. The method of claim 13, wherein the immunogenic protein comprises the amino acid sequence of SEQ ID NO.: 6.

17. The method of claim 13 further comprising a pharmaceutically acceptable carrier.

18. The method of claim 13 further comprising an adjuvant that is selected from the group consisting of alum, an unmethylated CpG motif, and dmLT.

\* \* \* \* \*

SEQUENCE LISTING

```
<160> NUMBER OF SEQ ID NOS: 11

<210> SEQ ID NO 1
<211> LENGTH: 4
<212> TYPE: PRT
<213> ORGANISM: Clostridium difficile

<400> SEQUENCE: 1

Gly Gly Ser Gly
1

<210> SEQ ID NO 2
<211> LENGTH: 4251
<212> TYPE: DNA
<213> ORGANISM: Clostridium difficile

<400> SEQUENCE: 2
atgagtttag ttaatagaaa acagttagaa aaaatggcaa atgtaagatt tcgtactcaa      60
gaagatgaat atgttgcaat attggatgct ttagaagaat atcataatat gtcagagaat     120
actgtagtcg aaaaatattt aaaattaaaa gatataaata gtttaacaga tatttatata     180
gatacatata aaaaatctgg tagaaataaa gccttaaaaa aatttaagga atatctagtt     240
acagaagtat tagagctaaa gaataataat ttaactccag ttgagaaaaa tttacatttt     300
gttgcgattg gaggtcaaat aaatgacact gctattaatt atataaatca atggaaagat     360
gtaaatagtg attataatgt taatgttttt tatgatagta atgcattttt gataaacaca     420
ttgaaaaaaa ctgtagtaga atcagcaata aatgatacac ttgaatcatt tagagaaaac     480
ttaaatgacc ctagatttga ctataataaa ttcttcagaa aacgtatgga aataatttat     540
gataaacaga aaatttcat aaactactat aaagctcaaa gagaagaaaa tcctgaactt     600
ataattgatg atattgtaaa gacatatctt tcaaatgagt attcaaagga gatagatgaa     660 cttaataccct atattgaaga atccttaaat aaaattacac agaatagtgg aaatgatgtt     720
agaaactttg aagaatttaa aaatggagag tcattcaact tatatgaaca agagttggta     780
gaaaggtgga atttagctgc tgcttctgac atattaagaa tatctgcatt aaaagaaatt     840
ggtggtatgt atttagatgt taatatgtta ccaggaatac aaccagactt atttgagtct     900
atagagaaac ctagttcagt aacagtggat ttttgggaaa tgacaaagtt agaagctata     960
atgaaataca aagaatatat accagaatat acctcagaac attttgacat gttagacgaa    1020
gaagttcaaa gtagttttga atctgttcta gcttctaagt cagataaatc agaaatattc    1080
tcatcacttg gtgatatgga ggcatcacca ctagaagtta aaattgcatt taatagtaag    1140
ggtattataa atcaagggct aatttctgtg aaagactcat attgtagcaa tttaatagta    1200
```

```
aaacaaatcg agaatagata taaaatattg aataatagtt taaatccagc tattagcgag    1260
gataatgatt ttaatactac aacgaatacc tttattgata gtataatggc tgaagctaat    1320
gcagataatg gtagatttat gatggaacta ggaaagtatt taagagttgg tttcttccca    1380
gatgttaaaa ctactattaa cttaagtggc cctgaagcat atgcggcagc ttatcaagat    1440
ttattaatgt ttaaagaagg cagtatgaat atccatttga tagaagctga tttaagaaac    1500
tttgaaatct ctaaaactaa tatttctcaa tcaactgaac aagaaatggc tagcttatgg    1560
tcatttgacg atgcaagagc taaagctcaa tttgaagaat ataaaaggaa ttattttgaa    1620
ggttctcttg gtgaagatga taatcttgat ttttctcaaa atatagtagt tgacaaggag    1680
tatcttttag aaaaaatatc ttcattagca agaagttcag agagaggata tatacactat    1740
attgttcagt tacaaggaga taaaattagt tatgaagcag catgtaactt atttgcaaag    1800
actccttatg atagtgtact gtttcagaaa aatatagaag attcagaaat tgcatattat    1860
tataatcctg gagatggtga aatacaagaa atagacaagt ataaaattcc aagtataatt    1920
tctgatagac ctaagattaa attaacattt attggtcatg gtaaagatga atttaatact    1980
gatatatttg caggttttga tgtagattca ttatccacag aaatagaagc agcaatagat    2040
ttagctaaag aggatatttc tcctaagtca atagaaataa atttattagg agctaatatg    2100
tttagctact ctatcaacgt agaggagact tatcctggaa aattattact taaagttaaa    2160
gataaaatat cagaattaat gccatctata agtcaagact ctattatagt aagtgcaaat    2220
caatatgaag ttagaataaa tagtgaagga agaagagaat tattggatca ttctggtgaa    2280
tggataaata aagaagaaag tggtggctct ggtataactg gatttgtgac tgtaggcgat    2340
gataaatact actttaatcc aattaatggt ggagctgctt caattggaga gacaataatt    2400
gatgacaaaa attattattt caaccaaagt ggagtgttac aaacaggtgt atttagtaca    2460
gaagatggat ttaaatattt tgccccagct aatacacttg atgaaaacct agaaggagaa    2520
gcaattgatt ttactggaaa attaattatt gacgaaaata tttattattt tgatgataat    2580
tatagaggag ctgtagaatg gaaagaatta gatggtgaaa tgcactattt tagcccagaa    2640
acaggtaaag ctttttaaagg tctaaatcaa ataggtgatt ataaatacta tttcaattct    2700
gatggagtta tgcaaaaagg atttgttagt ataaatgata taaacacta ttttgatgat    2760 tctggtgtta tgaaagtagg ttacactgaa atagatggca agcatttcta ctttgctgaa    2820
aacggagaaa tgcaaatagg agtatttaat acagaagatg gatttaaata ttttgctcat    2880
cataatgaag atttaggaaa tgaagaaggt gaagaaatct caggtggctc tggtaaaatg    2940
gtaacaggag tatttaaagg acctaatgga tttgagtatt ttgcacctgc taatactcac    3000
aataataaca tagaaggtca ggctatagtt taccagaaca aattcttaac tttgaatggc    3060
aaaaaatatt attttgataa tgactcaaaa gcagttactg gatggcaaac cattgatggt    3120
aaaaaatatt actttaatct taacactgct gaagcagcta ctggatggca aactattgat    3180
ggtaaaaaat attactttaa tcttaacact gctgaagcag ctactggatg gcaaactatt    3240
gatggtaaaa atattacttt aatactaac actttcatag cctcaactgg ttatacaagt    3300
attaatggta acattttta ttttaatact gatggtatta tgcagatagg agtgtttaaa    3360
ggacctaatg gatttgaata ctttgcacct gctaatacgg atgctaacaa catagaaggt    3420
caagctatac tttaccaaaa taattcttta actttgaatg gtaaaaaata ttactttggt    3480
agtgactcaa aagcagttac cggactgcga actattgatg gtaaaaaata ttactttaat    3540
actaacactg ctgttgcagt tactggatgg caaactatta atggtaaaaa atactacttt    3600
```

-continued

```
aatactaaca cttctatagc ttcaactggt tatacaatta ttagtggtaa acatttttat     3660
tttaatactg atggtattat gcagatagga gtgtttaaag gacctgatgg atttgaatac     3720
tttgcacctg ctaatacaga tgctaacaat atagaaggtc aagctatacg ttatcaaaat     3780
agattcctat atttacatga caatatatat tattttggta ataattcaaa agcggctact     3840
ggttgggtaa ctattgatgg taatagatat tacttcgagc ctaatacagc tatgggtgcg     3900
aatggttata aaactattga taataaaaat ttttacttta gaaatggttt acctcagata     3960
ggagtgttta aagggtctaa tggatttgaa tactttgcac ctgctaatac ggatgctaac     4020
aatatagaag gtcaagctat acgttatcaa aatagattcc tacatttact tggaaaaata     4080
tattactttg gtaataattc aaaagcagtt actggatggc aaactattaa tggtaaagta     4140
tattacttta tgcctgatac tgctatggct gcagctggtg acttttcga gattgatggt      4200 gttatatatt tctttggtgt tgatggagta aaagcccctg ggatatatgg g              4251
```

<210> SEQ ID NO 3
<211> LENGTH: 5745
<212> TYPE: DNA
<213> ORGANISM: Clostridium difficile

<400> SEQUENCE: 3

```
atgagtttag ttaatagaaa acagttagaa aaaatggcaa atgtaagatt tcgtactcaa       60
gaagatgaat atgttgcaat attggatgct ttagaagaat atcataatat gtcagagaat      120
actgtagtcg aaaaatattt aaaattaaaa gatataaata gtttaacaga tatttatata      180
gatacatata aaaaatctgg tagaaataaa gccttaaaaa aatttaagga atatctagtt      240
acagaagtat tagagctaaa gaataataat ttaactccag ttgagaaaaa tttacatttt      300
gttgcgattg gaggtcaaat aaatgacact gctattaatt atataaatca atggaaagat      360
gtaaatagtg attataatgt taatgttttt tatgatagta atgcattttt gataaacaca      420
ttgaaaaaaa ctgtagtaga atcagcaata aatgatacac ttgaatcatt tagagaaaac      480
ttaaatgacc ctagatttga ctataataaa ttcttcagaa aacgtatgga ataatttat       540 gataaacaga aaaatttcat aaactactat aaagctcaaa gagaagaaaa tcctgaactt      600
ataattgatg atattgtaaa gacatatctt tcaaatgagt attcaaagga gatagatgaa      660
cttaatacct atattgaaga atccttaaat aaaattacac agaatagtgg aaatgatgtt      720
agaaactttg aagaatttaa aaatggagag tcattcaact tatatgaaca agagttggta      780
gaaaggtgga atttagctgc tgcttctgac atattaagaa tatctgcatt aaaagaaatt      840
ggtggtatgt atttagatgt taatatgtta ccaggaatac aaccagactt atttgagtct      900
atagagaaac tagttcagt aacagtggat ttttgggaaa tgacaaagtt agaagctata      960
atgaaataca agaatatat accagaatat acctcagaac attttgacat gttagacgaa     1020
gaagttcaaa gtagttttga atctgttcta gcttctaagt cagataaatc agaaatattc     1080
tcatcacttg gtgatatgga ggcatcacca ctagaagtta aaattgcatt aatagtaag      1140 ggtattataa atcaagggct aatttctgtg aaagactcat attgtagcaa tttaatagta     1200
aaacaaatcg agaatagata taaaatattg aataatagtt aaatccagc tattagcgag     1260 gataatgatt ttaatactac aacgaatacc tttattgata gtataatggc tgaagctaat     1320
gcagataatg gtagatttat gatggaacta ggaaagtatt taagagttgg tttcttccca     1380
gatgttaaaa ctactattaa cttaagtggc cctgaagcat atgcggcagc ttatcaagat     1440
```

```
ttattaatgt ttaaagaagg cagtatgaat atccatttga tagaagctga tttaagaaac    1500
tttgaaatct ctaaaactaa tatttctcaa tcaactgaac aagaaatggc tagcttatgg    1560
tcatttgacg atgcaagagc taaagctcaa tttgaagaat ataaaaggaa ttattttgaa    1620
ggttctcttg gtgaagatga taatcttgat ttttctcaaa atatagtagt tgacaaggag    1680
tatcttttag aaaaaatatc ttcattagca agaagttcag agagaggata tatacactat    1740
attgttcagt tacaaggaga taaaattagt tatgaagcag catgtaactt atttgcaaag    1800
actccttatg atagtgtact gtttcagaaa aatatagaag attcagaaat tgcatattat    1860
tataatcctg gagatggtga aatacaagaa atagacaagt ataaaattcc aagtataatt    1920
tctgatagac ctaagattaa attaacattt attggtcatg gtaaagatga atttaatact    1980
gatatatttg caggttttga tgtagattca ttatccacag aaatagaagc agcaatagat    2040
ttagctaaag aggatatttc tcctaagtca atagaaataa atttattagg agctaatatg    2100
tttagctact ctatcaacgt agaggagact tatcctggaa aattattact taaagttaaa    2160
gataaaatat cagaattaat gccatctata agtcaagact ctattatagt aagtgcaaat    2220
caatatgaag ttagaataaa tagtgaagga agaagagaat tattggatca ttctggtgaa    2280
tggataaata agaagaaag tggtggctct ggtataactg gatttgtgac tgtaggcgat    2340
gataaatact actttaatcc aattaatggt ggagctgctt caattggaga gacaataatt    2400
gatgacaaaa attattattt caaccaaagt ggagtgttac aaacaggtgt atttagtaca    2460
gaagatggat ttaaatattt tgccccagct aatacacttg atgaaaacct agaaggagaa    2520
gcaattgatt ttactggaaa attaattatt gacgaaaata tttattattt tgatgataat    2580
tatagaggag ctgtagaatg gaaagaatta gatggtgaaa tgcactattt tagcccagaa    2640
acaggtaaag cttttaaagg tctaaatcaa ataggtgatt ataaatacta tttcaattct    2700
gatggagtta tgcaaaaagg atttgttagt ataaatgata taaacactta ttttgatgat    2760
tctggtgtta tgaaagtagg ttacactgaa atagatggca agcatttcta ctttgctgaa    2820
aacggagaaa tgcaaatagg agtatttaat acagaagatg gatttaaata ttttgctcat    2880
cataatgaag atttaggaaa tgaagaaggt gaagaaatct caggtggctc tggtaaaatg    2940
gtaacaggag tatttaaagg acctaatgga tttgagtatt ttgcacctgc taatactcac    3000
aataataaca tagaaggtca ggctatagtt taccagaaca aattcttaac tttgaatggc    3060
aaaaaatatt attttgataa tgactcaaaa gcagttactg atggcaaaac cattgatggt    3120
aaaaaatatt actttaatct taacactgct gaagcagcta ctggatggca aactattgat    3180
ggtaaaaaat attactttaa tcttaacact gctgaagcag ctactggatg gcaaactatt    3240
gatggtaaaa aatattactt taatactaac actttcatag cctcaactgg ttatacaagt    3300
attaatggta acattttta ttttaatact gatggtatta tgcagatagg agtgttaaa    3360 ggacctaatg gatttgaata ctttgcacct gctaatacgg atgctaacaa catagaaggt    3420
caagctatac tttaccaaaa taattcttta actttgaatg gtaaaaaata ttactttggt    3480
agtgactcaa aagcagttac cggactgcga actattgatg gtaaaaaata ttactttaat    3540
actaacactc tgttgcagt tactggatgg caaactatta tggtaaaaaa atactacttt    3600
aatactaaca cttctatagc ttcaactggt tatacaatta ttagtggtaa acatttttat    3660
tttaatactg atggtattat gcagatagga gtgtttaaag gacctgatgg atttgaatac    3720
tttgcacctg ctaatacaga tgctaacaat atagaaggtc aagctatacg ttatcaaaat    3780
agattcctat atttacatga caatatatat tattttggta ataattcaaa agcggctact    3840
```

-continued

```
ggttgggtaa ctattgatgg taatagatat tacttcgagc ctaatacagc tatgggtgcg    3900
aatggttata aaactattga taataaaaat ttttacttta gaaatggttt acctcagata    3960
ggagtgttta aagggtctaa tggatttgaa tactttgcac ctgctaatac ggatgctaac    4020
aatatagaag gtcaagctat acgttatcaa aatagattcc tacatttact tggaaaaata    4080
tattactttg gtaataattc aaaagcagtt actggatggc aaactattaa tggtaaagta    4140
tattacttta tgcctgatac tgctatggct gcagctggtg acttttcga gattgatggt    4200 gttatatatt tctttggtgt tgatggagta aaagcccctg gatatatgg gggtggctct    4260 ggtgcacaag tcattaatac aaacagcctg tcgctgttga cccagaataa cctgaacaaa    4320
tcccagtccg ctctgggcac cgctatcgag cgtctgtctt ccggtctgcg tatcaacagc    4380
gcgaaagacg atgcggcagg tcaggcgatt gctaaccgtt ttaccgcgaa catcaaaggt    4440
ctgactcagg cttcccgtaa cgctaacgac ggtatctcca ttgcgcagac cactgaaggc    4500
gcgctgaacg aaatcaacaa caacctgcag cgtgtgcgtg aactggcggt tcagtctgct    4560
aacagcacca actcccagtc tgacctcgac tccatccagg ctgaaatcac ccagcgcctg    4620
aacgaaatcg accgtgtatc cggccagact cagttcaacg gcgtgaaagt cctggcgcag    4680
gacaacaccc tgaccatcca ggttggtgcc aacgacggtg aaactatcga tatcgatctg    4740
aagcagatca actctcagac cctgggtctg gatacgctga atgtgcaaca aaaatataag    4800
gtcagcgata cggctgcaac tgttacagga tatgccgata ctacgattgc tttagacaat    4860 agtacttta aagcctcggc tactggtctt ggtggtactg accagaaaat tgatggcgat    4920
ttaaaatttg atgatacgac tggaaaatat tacgccaaag ttaccgttac gggggaact    4980 ggtaaagatg gctattatga agtttccgtt gataagacga acggtgaggt gactcttgct    5040
ggcggtgcga cttccccgct tacaggtgga ctacctgcga cagcaactga ggatgtgaaa    5100
aatgtccaag ttgcaaatgc tgatttgaca gaggctaaag ccgcattgac agcagcaggt    5160
gttaccggca cagcatctgt tgttaagatg tcttatactg ataataacgg taaaactatt    5220
gatggtggtt tagcagttaa ggtaggcgat gattactatt ctgcaactca aaataaagat    5280
ggttccataa gtattaatac tacgaaatac actgcagatg acggtacatc caaaactgca    5340
ctaaacaaac tgggtggcgc agacggcaaa accgaagttg tttctattgg tggtaaaact    5400
tacgctgcaa gtaaagccga aggtcacaac tttaaagcac agcctgatct ggcggaagcg    5460
gctgctacaa ccaccgaaaa cccgctgcag aaaattgatg ctgctttggc acaggttgac    5520
acgttacgtt ctgacctggg tgcggtacag aaccgtttca actccgctat taccaacctg    5580
ggcaacaccg taaacaacct gacttctgcc cgtagccgta tcgaagattc cgactacgcg    5640
accgaagttt ccaacatgtc tcgcgcgcag attctgcagc aggccggtac ctccgttctg    5700
gcgcaggcga accaggttcc gcaaaacgtc ctctctttac tgcgt              5745
```

<210> SEQ ID NO 4
<211> LENGTH: 5124
<212> TYPE: DNA
<213> ORGANISM: Clostridium difficile

<400> SEQUENCE: 4

```
atgagtttag ttaatagaaa acagttagaa aaaatggcaa atgtaagatt tcgtactcaa      60
gaagatgaat atgttgcaat attggatgct ttagaagaat atcataatat gtcagagaat     120
actgtagtcg aaaaatattt aaaattaaaa gatataaata gtttaacaga tatttatata     180
```

```
gatacatata aaaaatctgg tagaaataaa gccttaaaaa aatttaagga atatctagtt      240
acagaagtat tagagctaaa gaataataat ttaactccag ttgagaaaaa tttacatttt      300
gttgcgattg gaggtcaaat aaatgacact gctattaatt atataaatca atggaaagat      360
gtaaatagtg attataatgt taatgttttt tatgatagta atgcattttt gataaacaca      420
ttgaaaaaaa ctgtagtaga atcagcaata aatgatacac ttgaatcatt tagagaaaac      480
ttaaatgacc ctagatttga ctataataaa ttcttcagaa aacgtatgga ataatttat       540 gataaacaga aaaatttcat aaactactat aaagctcaaa gagaagaaaa tcctgaactt      600
ataattgatg atattgtaaa gacatatctt tcaaatgagt attcaaagga gatagatgaa      660
cttaatacct atattgaaga atccttaaat aaaattacac agaatagtgg aaatgatgtt      720
agaaactttg aagaatttaa aaatggagag tcattcaact tatatgaaca agagttggta      780
gaaaggtgga atttagctgc tgcttctgac atattaagaa tatctgcatt aaaagaaatt      840
ggtggtatgt atttagatgt taatatgtta ccaggaatac aaccagactt atttgagtct      900
atagagaaac ctagttcagt aacagtggat ttttgggaaa tgacaaagtt agaagctata      960
atgaaataca aagaatatat accagaatat acctcagaac attttgacat gttagacgaa     1020
gaagttcaaa gtagttttga atctgttcta gcttctaagt cagataaatc agaaatattc     1080
tcatcacttg gtgatatgga ggcatcacca ctagaagtta aaattgcatt taatagtaag     1140
ggtattataa atcaagggct aatttctgtg aaagactcat attgtagcaa tttaatagta     1200
aaacaaatcg agaatagata taaaatattg aataatagtt taaatccagc tattagcgag     1260
gataatgatt ttaatactac aacgaatacc tttattgata gtaataatggc tgaagctaat     1320 gcagataatg gtagatttat gatggaacta ggaaagtatt taagagttgg tttcttccca     1380
gatgttaaaa ctactattaa cttaagtggc cctgaagcat atgcggcagc ttatcaagat     1440
ttattaatgt ttaaagaagg cagtatgaat atccatttga tagaagctga tttaagaaac     1500
tttgaaatct ctaaaactaa tatttctcaa tcaactgaac aagaaatggc tagcttatgg     1560
tcatttgacg atgcaagagc taaagctcaa tttgaagaat ataaaaggaa ttattttgaa     1620
ggttctcttg gtgaagatga taatcttgat ttttctcaaa atatagtagt tgacaaggag     1680
tatcttttag aaaaaatatc ttcattagca agaagttcag agagaggata tatacactat     1740
attgttcagt tacaaggaga taaaattagt tatgaagcag catgtaactt atttgcaaag     1800
actccttatg atagtgtact gtttcagaaa aatatagaag attcagaaat tgcatattat     1860
tataatcctg gagatggtga aatacaagaa atagacaagt ataaaattcc aagtataatt     1920
tctgatagac ctaagattaa attaacattt attggtcatg gtaaagatga atttaatact     1980
gatatatttg caggttttga tgtagattca ttatccacag aaatagaagc agcaatagat     2040
ttagctaaag aggatatttc tcctaagtca atagaaataa atttattagg agctaatatg     2100
tttagctact ctatcaacgt agaggagact tatcctggaa aattattact taaagttaaa     2160
gataaaatat cagaattaat gccatctata agtcaagact ctattatagt aagtgcaaat     2220
caatatgaag ttagaataaa tagtgaagga agaagagaat tattggatca ttctggtgaa     2280
tggataaata agaagaaag tggtggctct ggtaaaatgg taacaggagt atttaaagga      2340
cctaatggat ttgagtattt tgcacctgct aatactcaca ataataacat agaaggtcag     2400
gctatagttt accagaacaa attcttaact ttgaatggca aaaaatatta ttttgataat     2460
gactcaaaag cagttactgg atggcaaacc attgatggta aaaaatatta ctttaatctt     2520
aacactgctg aagcagctac tggatggcaa actattgatg gtaaaaaata ttactttaat     2580
```

```
cttaacactg ctgaagcagc tactggatgg caaactattg atggtaaaaa atattacttt    2640
aatactaaca ctttcatagc ctcaactggt tatacaagta ttaatggtaa acattttat    2700 tttaatactg atggtattat gcagatagga gtgtttaaag gacctaatgg atttgaatac    2760
tttgcacctg ctaatacgga tgctaacaac atagaaggtc aagctatact ttaccaaaat    2820
aaattcttaa ctttgaatgg taaaaaatat tactttggta gtgactcaaa agcagttacc    2880
ggactgcgaa ctattgatgg taaaaaatat tactttaata ctaacactgc tgttgcagtt    2940
actggatggc aaactattaa tggtaaaaaa tactactttta atactaacac ttctatagct    3000
tcaactggtt atacaattat tagtggtaaa cattttatt ttaatactga tggtattatg    3060
cagataggag tgtttaaagg acctgatgga tttgaatact ttgcacctgc taatacagat    3120
gctaacaata tagaaggtca agctatacgt tatcaaaata gattcctata tttcatgac    3180 aatatatatt attttggtaa taattcaaaa gcggctactg gttgggtaac tattgatggt    3240
aatagatatt acttcgagcc taatacagct atgggtgcga atggttataa aactattgat    3300
aataaaaatt tttactttag aaatggttta cctcagatag gagtgtttaa agggtctaat    3360
ggatttgaat acttttgcacc tgctaatacg atgctaaca atatagaagg tcaagctata    3420
cgttatcaaa atagattcct acatttactt ggaaaaatat attactttgg taataattca    3480
aaagcagtta ctggatggca aactattaat ggtaaagtat attactttat gcctgatact    3540
gctatggctg cagctggtgg acttttcgag attgatggtg ttatatattt ctttggtgtt    3600
gatggagtaa aagcccctgg gatatatggg ggtggctctg gtgcacaagt cattaataca    3660
aacagcctgt cgctgttgac ccagaataac ctgaacaaat cccagtccgc tctgggcacc    3720
gctatcgagc gtctgtcttc cggtctgcgt atcaacagcg cgaaagacga tgcggcaggt    3780
caggcgattg ctaaccgttt taccgcgaac atcaaaggtc tgactcaggc ttcccgtaac    3840
gctaacgacg gtatctccat tgcgcagacc actgaaggcg cgctgaacga atcaacaac    3900 aacctgcagc gtgtgcgtga actggcggtt cagtctgcta acagcaccaa ctcccagtct    3960
gacctcgact ccatccaggc tgaaatcacc cagcgcctga cgaaatcga ccgtgtatcc    4020 ggccagactc agttcaacgg cgtgaaagtc ctggcgcagg acaacaccct gaccatccag    4080
gttggtgcca acgacggtga aactatcgat atcgatctga gcagatcaa ctctcagacc    4140 ctgggtctgg atacgctgaa tgtgcaacaa aaatataagg tcagcgatac ggctgcaact    4200
gttacaggat atgccgatac tacgattgct ttagacaata gtactttaa agcctcggct    4260 actggtcttg gtggtactga ccagaaaatt gatggcgatt taaatttga tgatacgact    4320 ggaaaatatt acgccaaagt taccgttacg gggggaactg gtaaagatgg ctattatgaa    4380
gtttccgttg ataagacgaa cggtgaggtg actcttgctg gcggtgcgac ttccccgctt    4440
acaggtggac tacctgcgac agcaactgag gatgtgaaaa atgtccaagt tgcaaatgct    4500
gatttgacag aggctaaagc cgcattgaca gcagcaggtg ttaccggcac agcatctgtt    4560
gttaagatgt cttatactga taataacggt aaaactattg atggtggttt agcagttaag    4620
gtaggcgatg attactattc tgcaactcaa aataaagatg gttccataag tattaatact    4680
acgaaataca ctgcagatga cggtacatcc aaaactgcac taaacaaact gggtggcgca    4740
gacggcaaaa ccgaagttgt ttctattggt ggtaaaactt acgctgcaag taaagccgaa    4800
ggtcacaact ttaaagcaca gcctgatctg cgggaagcgg ctgctacaac caccgaaaac    4860
ccgctgcaga aaattgatgc tgctttggca caggttgaca cgttacgttc tgacctgggt    4920
```

```
gcggtacaga accgtttcaa ctccgctatt accaacctgg gcaacaccgt aaacaacctg    4980
acttctgccc gtagccgtat cgaagattcc gactacgcga ccgaagtttc aacatgtct     5040 cgcgcgcaga ttctgcagca ggccggtacc tccgttctgg cgcaggcgaa ccaggttccg    5100
caaaacgtcc tctctttact gcgt                                           5124
```

<210> SEQ ID NO 5
<211> LENGTH: 1417
<212> TYPE: PRT
<213> ORGANISM: Clostridium difficile

<400> SEQUENCE: 5

```
Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
            20                  25                  30

Glu Tyr His Asn Met Ser Glu Asn Thr Val Val Glu Lys Tyr Leu Lys
        35                  40                  45

Leu Lys Asp Ile Asn Ser Leu Thr Asp Ile Tyr Ile Asp Thr Tyr Lys
    50                  55                  60

Lys Ser Gly Arg Asn Lys Ala Leu Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Ala Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
            180                 185                 190

Gln Arg Glu Glu Asn Pro Glu Leu Ile Ile Asp Asp Ile Val Lys Thr
        195                 200                 205

Tyr Leu Ser Asn Glu Tyr Ser Lys Glu Ile Asp Glu Leu Asn Thr Tyr
    210                 215                 220

Ile Glu Glu Ser Leu Asn Lys Ile Thr Gln Asn Ser Gly Asn Asp Val
225                 230                 235                 240

Arg Asn Phe Glu Glu Phe Lys Asn Gly Glu Ser Phe Asn Leu Tyr Glu
                245                 250                 255

Gln Glu Leu Val Glu Arg Trp Asn Leu Ala Ala Ala Ser Asp Ile Leu
            260                 265                 270

Arg Ile Ser Ala Leu Lys Glu Ile Gly Gly Met Tyr Leu Asp Val Asn
        275                 280                 285

Met Leu Pro Gly Ile Gln Pro Asp Leu Phe Glu Ser Ile Glu Lys Pro
    290                 295                 300

Ser Ser Val Thr Val Asp Phe Trp Glu Met Thr Lys Leu Glu Ala Ile
305                 310                 315                 320

Met Lys Tyr Lys Glu Tyr Ile Pro Glu Tyr Thr Ser Glu His Phe Asp
                325                 330                 335
```

```
Met Leu Asp Glu Val Gln Ser Ser Phe Glu Ser Val Leu Ala Ser
            340                 345                 350
Lys Ser Asp Lys Ser Glu Ile Phe Ser Ser Leu Gly Asp Met Glu Ala
        355                 360                 365
Ser Pro Leu Glu Val Lys Ile Ala Phe Asn Ser Lys Gly Ile Ile Asn
    370                 375                 380
Gln Gly Leu Ile Ser Val Lys Asp Ser Tyr Cys Ser Asn Leu Ile Val
385                 390                 395                 400
Lys Gln Ile Glu Asn Arg Tyr Lys Ile Leu Asn Asn Ser Leu Asn Pro
                405                 410                 415
Ala Ile Ser Glu Asp Asn Asp Phe Asn Thr Thr Thr Asn Thr Phe Ile
            420                 425                 430
Asp Ser Ile Met Ala Glu Ala Asn Ala Asp Asn Gly Arg Phe Met Met
        435                 440                 445
Glu Leu Gly Lys Tyr Leu Arg Val Gly Phe Phe Pro Asp Val Lys Thr
    450                 455                 460
Thr Ile Asn Leu Ser Gly Pro Glu Ala Tyr Ala Ala Tyr Gln Asp
465                 470                 475                 480
Leu Leu Met Phe Lys Glu Gly Ser Met Asn Ile His Leu Ile Glu Ala
                485                 490                 495
Asp Leu Arg Asn Phe Glu Ile Ser Lys Thr Asn Ile Ser Gln Ser Thr
            500                 505                 510
Glu Gln Glu Met Ala Ser Leu Trp Ser Phe Asp Asp Ala Arg Ala Lys
        515                 520                 525
Ala Gln Phe Glu Glu Tyr Lys Arg Asn Tyr Phe Glu Gly Ser Leu Gly
    530                 535                 540
Glu Asp Asp Asn Leu Asp Phe Ser Gln Asn Ile Val Val Asp Lys Glu
545                 550                 555                 560
Tyr Leu Leu Glu Lys Ile Ser Ser Leu Ala Arg Ser Ser Glu Arg Gly
                565                 570                 575
Tyr Ile His Tyr Ile Val Gln Leu Gln Gly Asp Lys Ile Ser Tyr Glu
            580                 585                 590
Ala Ala Cys Asn Leu Phe Ala Lys Thr Pro Tyr Asp Ser Val Leu Phe
        595                 600                 605
Gln Lys Asn Ile Glu Asp Ser Glu Ile Ala Tyr Tyr Tyr Asn Pro Gly
    610                 615                 620
Asp Gly Glu Ile Gln Glu Ile Asp Lys Tyr Lys Ile Pro Ser Ile Ile
625                 630                 635                 640
Ser Asp Arg Pro Lys Ile Lys Leu Thr Phe Ile Gly His Gly Lys Asp
                645                 650                 655
Glu Phe Asn Thr Asp Ile Phe Ala Gly Phe Asp Val Asp Ser Leu Ser
            660                 665                 670
Thr Glu Ile Glu Ala Ala Ile Asp Leu Ala Lys Glu Asp Ile Ser Pro
        675                 680                 685
Lys Ser Ile Glu Ile Asn Leu Leu Gly Ala Asn Met Phe Ser Tyr Ser
    690                 695                 700
Ile Asn Val Glu Glu Thr Tyr Pro Gly Lys Leu Leu Leu Lys Val Lys
705                 710                 715                 720
Asp Lys Ile Ser Glu Leu Met Pro Ser Ile Ser Gln Asp Ser Ile Ile
                725                 730                 735
Val Ser Ala Asn Gln Tyr Glu Val Arg Ile Asn Ser Glu Gly Arg Arg
            740                 745                 750
Glu Leu Leu Asp His Ser Gly Glu Trp Ile Asn Lys Glu Glu Ser Gly
```

-continued

```
            755                 760                 765
Gly Ser Gly Ile Thr Gly Phe Val Thr Val Gly Asp Asp Lys Tyr Tyr
    770                 775                 780
Phe Asn Pro Ile Asn Gly Gly Ala Ala Ser Ile Gly Glu Thr Ile Ile
785                 790                 795                 800
Asp Asp Lys Asn Tyr Tyr Phe Asn Gln Ser Gly Val Leu Gln Thr Gly
                805                 810                 815
Val Phe Ser Thr Glu Asp Gly Phe Lys Tyr Phe Ala Pro Ala Asn Thr
                820                 825                 830
Leu Asp Glu Asn Leu Glu Gly Glu Ala Ile Asp Phe Thr Gly Lys Leu
                835                 840                 845
Ile Ile Asp Glu Asn Ile Tyr Tyr Phe Asp Asn Tyr Arg Gly Ala
    850                 855                 860
Val Glu Trp Lys Glu Leu Asp Gly Glu Met His Tyr Phe Ser Pro Glu
865                 870                 875                 880
Thr Gly Lys Ala Phe Lys Gly Leu Asn Gln Ile Gly Asp Tyr Lys Tyr
                885                 890                 895
Tyr Phe Asn Ser Asp Gly Val Met Gln Lys Gly Phe Val Ser Ile Asn
                900                 905                 910
Asp Asn Lys His Tyr Phe Asp Asp Ser Gly Val Met Lys Val Gly Tyr
                915                 920                 925
Thr Glu Ile Asp Gly Lys His Phe Tyr Phe Ala Glu Asn Gly Glu Met
                930                 935                 940
Gln Ile Gly Val Phe Asn Thr Glu Asp Gly Phe Lys Tyr Phe Ala His
945                 950                 955                 960
His Asn Glu Asp Leu Gly Asn Glu Glu Gly Glu Ile Ser Gly Gly
                965                 970                 975
Ser Gly Lys Met Val Thr Gly Val Phe Lys Gly Pro Asn Gly Phe Glu
                980                 985                 990
Tyr Phe Ala Pro Ala Asn Thr His Asn Asn Asn Ile Glu Gly Gln Ala
                995                 1000                1005
Ile Val Tyr Gln Asn Lys Phe Leu Thr Leu Asn Gly Lys Lys Tyr
    1010                1015                1020
Tyr Phe Asp Asn Asp Ser Lys Ala Val Thr Gly Trp Gln Thr Ile
    1025                1030                1035
Asp Gly Lys Lys Tyr Tyr Phe Asn Leu Asn Thr Ala Glu Ala Ala
    1040                1045                1050
Thr Gly Trp Gln Thr Ile Asp Gly Lys Lys Tyr Tyr Phe Asn Leu
    1055                1060                1065
Asn Thr Ala Glu Ala Ala Thr Gly Trp Gln Thr Ile Asp Gly Lys
    1070                1075                1080
Lys Tyr Tyr Phe Asn Thr Asn Thr Phe Ile Ala Ser Thr Gly Tyr
    1085                1090                1095
Thr Ser Ile Asn Gly Lys His Phe Tyr Phe Asn Thr Asp Gly Ile
    1100                1105                1110
Met Gln Ile Gly Val Phe Lys Gly Pro Asn Gly Phe Glu Tyr Phe
    1115                1120                1125
Ala Pro Ala Asn Thr Asp Ala Asn Asn Ile Glu Gly Gln Ala Ile
    1130                1135                1140
Leu Tyr Gln Asn Lys Phe Leu Thr Leu Asn Gly Lys Lys Tyr Tyr
    1145                1150                1155
Phe Gly Ser Asp Ser Lys Ala Val Thr Gly Leu Arg Thr Ile Asp
    1160                1165                1170
```

```
Gly Lys Lys Tyr Tyr Phe Asn Thr Asn Thr Ala Val Ala Val Thr
    1175                1180                1185

Gly Trp Gln Thr Ile Asn Gly Lys Lys Tyr Tyr Phe Asn Thr Asn
    1190                1195                1200

Thr Ser Ile Ala Ser Thr Gly Tyr Thr Ile Ile Ser Gly Lys His
    1205                1210                1215

Phe Tyr Phe Asn Thr Asp Gly Ile Met Gln Ile Gly Val Phe Lys
    1220                1225                1230

Gly Pro Asp Gly Phe Glu Tyr Phe Ala Pro Ala Asn Thr Asp Ala
    1235                1240                1245

Asn Asn Ile Glu Gly Gln Ala Ile Arg Tyr Gln Asn Arg Phe Leu
    1250                1255                1260

Tyr Leu His Asp Asn Ile Tyr Tyr Phe Gly Asn Asn Ser Lys Ala
    1265                1270                1275

Ala Thr Gly Trp Val Thr Ile Asp Gly Asn Arg Tyr Tyr Phe Glu
    1280                1285                1290

Pro Asn Thr Ala Met Gly Ala Asn Gly Tyr Lys Thr Ile Asp Asn
    1295                1300                1305

Lys Asn Phe Tyr Phe Arg Asn Gly Leu Pro Gln Ile Gly Val Phe
    1310                1315                1320

Lys Gly Ser Asn Gly Phe Glu Tyr Phe Ala Pro Ala Asn Thr Asp
    1325                1330                1335

Ala Asn Asn Ile Glu Gly Gln Ala Ile Arg Tyr Gln Asn Arg Phe
    1340                1345                1350

Leu His Leu Leu Gly Lys Ile Tyr Tyr Phe Gly Asn Asn Ser Lys
    1355                1360                1365

Ala Val Thr Gly Trp Gln Thr Ile Asn Gly Lys Val Tyr Tyr Phe
    1370                1375                1380

Met Pro Asp Thr Ala Met Ala Ala Ala Gly Gly Leu Phe Glu Ile
    1385                1390                1395

Asp Gly Val Ile Tyr Phe Phe Gly Val Asp Gly Val Lys Ala Pro
    1400                1405                1410

Gly Ile Tyr Gly
    1415

<210> SEQ ID NO 6
<211> LENGTH: 1915
<212> TYPE: PRT
<213> ORGANISM: Clostridium difficile

<400> SEQUENCE: 6

Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
            20                  25                  30

Glu Tyr His Asn Met Ser Glu Asn Thr Val Val Glu Lys Tyr Leu Lys
        35                  40                  45

Leu Lys Asp Ile Asn Ser Leu Thr Asp Ile Tyr Ile Asp Thr Tyr Lys
    50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Ala Ile Gly Gly Gln Ile Asn Asp Thr Ala Ile
```

```
            100                 105                 110
Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
            180                 185                 190

Gln Arg Glu Glu Asn Pro Glu Leu Ile Ile Asp Asp Ile Val Lys Thr
        195                 200                 205

Tyr Leu Ser Asn Glu Tyr Ser Lys Glu Ile Asp Glu Leu Asn Thr Tyr
    210                 215                 220

Ile Glu Glu Ser Leu Asn Lys Ile Thr Gln Asn Ser Gly Asn Asp Val
225                 230                 235                 240

Arg Asn Phe Glu Glu Phe Lys Asn Gly Glu Ser Phe Asn Leu Tyr Glu
                245                 250                 255

Gln Glu Leu Val Glu Arg Trp Asn Leu Ala Ala Ala Ser Asp Ile Leu
            260                 265                 270

Arg Ile Ser Ala Leu Lys Glu Ile Gly Gly Met Tyr Leu Asp Val Asn
        275                 280                 285

Met Leu Pro Gly Ile Gln Pro Asp Leu Phe Glu Ser Ile Glu Lys Pro
    290                 295                 300

Ser Ser Val Thr Val Asp Phe Trp Glu Met Thr Lys Leu Glu Ala Ile
305                 310                 315                 320

Met Lys Tyr Lys Glu Tyr Ile Pro Glu Tyr Thr Ser Glu His Phe Asp
                325                 330                 335

Met Leu Asp Glu Glu Val Gln Ser Ser Phe Glu Ser Val Leu Ala Ser
            340                 345                 350

Lys Ser Asp Lys Ser Glu Ile Phe Ser Ser Leu Gly Asp Met Glu Ala
        355                 360                 365

Ser Pro Leu Glu Val Lys Ile Ala Phe Asn Ser Lys Gly Ile Ile Asn
    370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Thr Asn Thr Phe Ile
            420                 425                 430

Asp Ser Ile Met Ala Glu Ala Asn Ala Asp Asn Gly Arg Phe Met Met
        435                 440                 445

Glu Leu Gly Lys Tyr Leu Arg Val Gly Phe Phe Pro Asp Val Lys Thr
    450                 455                 460

Thr Ile Asn Leu Ser Gly Pro Glu Ala Tyr Ala Ala Ala Tyr Gln Asp
465                 470                 475                 480

Leu Leu Met Phe Lys Glu Gly Ser Met Asn Ile His Leu Ile Glu Ala
                485                 490                 495

Asp Leu Arg Asn Phe Glu Ile Ser Lys Thr Asn Ile Ser Gln Ser Thr
            500                 505                 510

Glu Gln Glu Met Ala Ser Leu Trp Ser Phe Asp Asp Ala Arg Ala Lys
        515                 520                 525
```

```
Ala Gln Phe Glu Glu Tyr Lys Arg Asn Tyr Phe Gly Ser Leu Gly
    530                 535                 540

Glu Asp Asp Asn Leu Asp Phe Ser Gln Asn Ile Val Val Asp Lys Glu
545                 550                 555                 560

Tyr Leu Leu Glu Lys Ile Ser Ser Leu Ala Arg Ser Ser Glu Arg Gly
                565                 570                 575

Tyr Ile His Tyr Ile Val Gln Leu Gln Gly Asp Lys Ile Ser Tyr Glu
            580                 585                 590

Ala Ala Cys Asn Leu Phe Ala Lys Thr Pro Tyr Asp Ser Val Leu Phe
        595                 600                 605

Gln Lys Asn Ile Glu Asp Ser Glu Ile Ala Tyr Tyr Asn Pro Gly
    610                 615                 620

Asp Gly Glu Ile Gln Glu Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
                645                 650                 655

Glu Phe Asn Thr Asp Ile Phe Ala Gly Phe Asp Val Asp Ser Leu Ser
                660                 665                 670

Thr Glu Ile Glu Ala Ala Ile Asp Leu Ala Lys Glu Asp Ile Ser Pro
                675                 680                 685

Lys Ser Ile Glu Ile Asn Leu Leu Gly Ala Asn Met Phe Ser Tyr Ser
690                 695                 700

Ile Asn Val Glu Glu Thr Tyr Pro Gly Lys Leu Leu Leu Lys Val Lys
705                 710                 715                 720

Asp Lys Ile Ser Glu Leu Met Pro Ser Ile Ser Gln Asp Ser Ile Ile
                725                 730                 735

Val Ser Ala Asn Gln Tyr Glu Val Arg Ile Asn Ser Glu Gly Arg Arg
                740                 745                 750

Glu Leu Leu Asp His Ser Gly Glu Trp Ile Asn Lys Glu Glu Ser Gly
                755                 760                 765

Gly Ser Gly Ile Thr Gly Phe Val Thr Val Gly Asp Asp Lys Tyr Tyr
                770                 775                 780

Phe Asn Pro Ile Asn Gly Gly Ala Ala Ser Ile Gly Glu Thr Ile Ile
785                 790                 795                 800

Asp Asp Lys Asn Tyr Tyr Phe Asn Gln Ser Gly Val Leu Gln Thr Gly
                805                 810                 815

Val Phe Ser Thr Glu Asp Gly Phe Lys Tyr Phe Ala Pro Ala Asn Thr
                820                 825                 830

Leu Asp Glu Asn Leu Glu Gly Glu Ala Ile Asp Phe Thr Gly Lys Leu
                835                 840                 845

Ile Ile Asp Glu Asn Ile Tyr Tyr Phe Asp Asp Asn Tyr Arg Gly Ala
    850                 855                 860

Val Glu Trp Lys Glu Leu Asp Gly Glu Met His Tyr Phe Ser Pro Glu
865                 870                 875                 880

Thr Gly Lys Ala Phe Lys Gly Leu Asn Gln Ile Gly Asp Tyr Lys Tyr
                885                 890                 895

Tyr Phe Asn Ser Asp Gly Val Met Gln Lys Gly Phe Val Ser Ile Asn
                900                 905                 910

Asp Asn Lys His Tyr Phe Asp Asp Ser Gly Val Met Lys Val Gly Tyr
            915                 920                 925

Thr Glu Ile Asp Gly Lys His Phe Tyr Phe Ala Glu Asn Gly Glu Met
    930                 935                 940
```

```
Gln Ile Gly Val Phe Asn Thr Glu Asp Gly Phe Lys Tyr Phe Ala His
945                 950                 955                 960

His Asn Glu Asp Leu Gly Asn Glu Glu Gly Glu Glu Ile Ser Gly Gly
            965                 970                 975

Ser Gly Lys Met Val Thr Gly Val Phe Lys Gly Pro Asn Gly Phe Glu
        980                 985                 990

Tyr Phe Ala Pro Ala Asn Thr His  Asn Asn Asn Ile Glu Gly Gln Ala
        995                 1000                1005

Ile Val Tyr Gln Asn Lys Phe Leu Thr Leu Asn Gly Lys Lys Tyr
1010                1015                1020

Tyr Phe Asp Asn Asp Ser Lys Ala Val Thr Gly Trp Gln Thr Ile
1025                1030                1035

Asp Gly Lys Lys Tyr Tyr Phe Asn Leu Asn Thr Ala Glu Ala Ala
1040                1045                1050

Thr Gly Trp Gln Thr Ile Asp Gly Lys Lys Tyr Tyr Phe Asn Leu
1055                1060                1065

Asn Thr Ala Glu Ala Ala Thr Gly Trp Gln Thr Ile Asp Gly Lys
1070                1075                1080

Lys Tyr Tyr Phe Asn Thr Asn Thr Phe Ile Ala Ser Thr Gly Tyr
1085                1090                1095

Thr Ser Ile Asn Gly Lys His Phe Tyr Phe Asn Thr Asp Gly Ile
1100                1105                1110

Met Gln Ile Gly Val Phe Lys Gly Pro Asn Gly Phe Glu Tyr Phe
1115                1120                1125

Ala Pro Ala Asn Thr Asp Ala Asn Asn Ile Glu Gly Gln Ala Ile
1130                1135                1140

Leu Tyr Gln Asn Lys Phe Leu Thr Leu Asn Gly Lys Lys Tyr Tyr
1145                1150                1155

Phe Gly Ser Asp Ser Lys Ala Val Thr Gly Leu Arg Thr Ile Asp
1160                1165                1170

Gly Lys Lys Tyr Tyr Phe Asn Thr Asn Thr Ala Val Ala Val Thr
1175                1180                1185

Gly Trp Gln Thr Ile Asn Gly Lys Lys Tyr Tyr Phe Asn Thr Asn
1190                1195                1200

Thr Ser Ile Ala Ser Thr Gly Tyr Thr Ile Ile Ser Gly Lys His
1205                1210                1215

Phe Tyr Phe Asn Thr Asp Gly Ile Met Gln Ile Gly Val Phe Lys
1220                1225                1230

Gly Pro Asp Gly Phe Glu Tyr Phe Ala Pro Ala Asn Thr Asp Ala
1235                1240                1245

Asn Asn Ile Glu Gly Gln Ala Ile Arg Tyr Gln Asn Arg Phe Leu
1250                1255                1260

Tyr Leu His Asp Asn Ile Tyr Tyr Phe Gly Asn Asn Ser Lys Ala
1265                1270                1275

Ala Thr Gly Trp Val Thr Ile Asp Gly Asn Arg Tyr Tyr Phe Glu
1280                1285                1290

Pro Asn Thr Ala Met Gly Ala Asn Gly Tyr Lys Thr Ile Asp Asn
1295                1300                1305

Lys Asn Phe Tyr Phe Arg Asn Gly Leu Pro Gln Ile Gly Val Phe
1310                1315                1320

Lys Gly Ser Asn Gly Phe Glu Tyr Phe Ala Pro Ala Asn Thr Asp
1325                1330                1335

Ala Asn Asn Ile Glu Gly Gln Ala Ile Arg Tyr Gln Asn Arg Phe
```

-continued

```
                1340                1345                1350
Leu His Leu Leu Gly Lys Ile Tyr Tyr Phe Gly Asn Asn Ser Lys
    1355                1360                1365
Ala Val Thr Gly Trp Gln Thr Ile Asn Gly Lys Val Tyr Tyr Phe
    1370                1375                1380
Met Pro Asp Thr Ala Met Ala Ala Gly Gly Leu Phe Glu Ile
    1385                1390                1395
Asp Gly Val Ile Tyr Phe Phe Gly Val Asp Gly Val Lys Ala Pro
    1400                1405                1410
Gly Ile Tyr Gly Gly Gly Ser Gly Ala Gln Val Ile Asn Thr Asn
    1415                1420                1425
Ser Leu Ser Leu Leu Thr Gln Asn Asn Leu Asn Lys Ser Gln Ser
    1430                1435                1440
Ala Leu Gly Thr Ala Ile Glu Arg Leu Ser Ser Gly Leu Arg Ile
    1445                1450                1455
Asn Ser Ala Lys Asp Asp Ala Ala Gly Gln Ala Ile Ala Asn Arg
    1460                1465                1470
Phe Thr Ala Asn Ile Lys Gly Leu Thr Gln Ala Ser Arg Asn Ala
    1475                1480                1485
Asn Asp Gly Ile Ser Ile Ala Gln Thr Thr Glu Gly Ala Leu Asn
    1490                1495                1500
Glu Ile Asn Asn Asn Leu Gln Arg Val Arg Glu Leu Ala Val Gln
    1505                1510                1515
Ser Ala Asn Ser Thr Asn Ser Gln Ser Asp Leu Asp Ser Ile Gln
    1520                1525                1530
Ala Glu Ile Thr Gln Arg Leu Asn Glu Ile Asp Arg Val Ser Gly
    1535                1540                1545
Gln Thr Gln Phe Asn Gly Val Lys Val Leu Ala Gln Asp Asn Thr
    1550                1555                1560
Leu Thr Ile Gln Val Gly Ala Asn Asp Gly Glu Thr Ile Asp Ile
    1565                1570                1575
Asp Leu Lys Gln Ile Asn Ser Gln Thr Leu Gly Leu Asp Thr Leu
    1580                1585                1590
Asn Val Gln Gln Lys Tyr Lys Val Ser Asp Thr Ala Ala Thr Val
    1595                1600                1605
Thr Gly Tyr Ala Asp Thr Thr Ile Ala Leu Asp Asn Ser Thr Phe
    1610                1615                1620
Lys Ala Ser Ala Thr Gly Leu Gly Gly Thr Asp Gln Lys Ile Asp
    1625                1630                1635
Gly Asp Leu Lys Phe Asp Asp Thr Thr Gly Lys Tyr Tyr Ala Lys
    1640                1645                1650
Val Thr Val Thr Gly Gly Thr Gly Lys Asp Gly Tyr Tyr Glu Val
    1655                1660                1665
Ser Val Asp Lys Thr Asn Gly Glu Val Thr Leu Ala Gly Gly Ala
    1670                1675                1680
Thr Ser Pro Leu Thr Gly Gly Leu Pro Ala Thr Ala Thr Glu Asp
    1685                1690                1695
Val Lys Asn Val Gln Val Ala Asn Ala Asp Leu Thr Glu Ala Lys
    1700                1705                1710
Ala Ala Leu Thr Ala Ala Gly Val Thr Gly Thr Ala Ser Val Val
    1715                1720                1725
Lys Met Ser Tyr Thr Asp Asn Asn Gly Lys Thr Ile Asp Gly Gly
    1730                1735                1740
```

```
Leu Ala Val Lys Val Gly Asp Asp Tyr Tyr Ser Ala Thr Gln Asn
    1745                1750                1755

Lys Asp Gly Ser Ile Ser Ile Asn Thr Thr Lys Tyr Thr Ala Asp
    1760                1765                1770

Asp Gly Thr Ser Lys Thr Ala Leu Asn Lys Leu Gly Gly Ala Asp
    1775                1780                1785

Gly Lys Thr Glu Val Val Ser Ile Gly Gly Lys Thr Tyr Ala Ala
    1790                1795                1800

Ser Lys Ala Glu Gly His Asn Phe Lys Ala Gln Pro Asp Leu Ala
    1805                1810                1815

Glu Ala Ala Thr Thr Thr Glu Asn Pro Leu Gln Lys Ile Asp
    1820                1825                1830

Ala Ala Leu Ala Gln Val Asp Thr Leu Arg Ser Asp Leu Gly Ala
    1835                1840                1845

Val Gln Asn Arg Phe Asn Ser Ala Ile Thr Asn Leu Gly Asn Thr
    1850                1855                1860

Val Asn Asn Leu Thr Ser Ala Arg Ser Arg Ile Glu Asp Ser Asp
    1865                1870                1875

Tyr Ala Thr Glu Val Ser Asn Met Ser Arg Ala Gln Ile Leu Gln
    1880                1885                1890

Gln Ala Gly Thr Ser Val Leu Ala Gln Ala Asn Gln Val Pro Gln
    1895                1900                1905

Asn Val Leu Ser Leu Leu Arg
    1910                1915

<210> SEQ ID NO 7
<211> LENGTH: 1708
<212> TYPE: PRT
<213> ORGANISM: Clostridium difficile

<400> SEQUENCE: 7

Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
                20                  25                  30

Glu Tyr His Asn Met Ser Glu Asn Thr Val Val Glu Lys Tyr Leu Lys
            35                  40                  45

Leu Lys Asp Ile Asn Ser Leu Thr Asp Ile Tyr Ile Asp Thr Tyr Lys
        50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Ala Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
```

```
            180                 185                 190
Gln Arg Glu Glu Asn Pro Glu Leu Ile Ile Asp Asp Ile Val Lys Thr
            195                 200                 205

Tyr Leu Ser Asn Glu Tyr Ser Lys Glu Ile Asp Glu Leu Asn Thr Tyr
            210                 215                 220

Ile Glu Glu Ser Leu Asn Lys Ile Thr Gln Asn Ser Gly Asn Asp Val
225                 230                 235                 240

Arg Asn Phe Glu Glu Phe Lys Asn Gly Glu Ser Phe Asn Leu Tyr Glu
                245                 250                 255

Gln Glu Leu Val Glu Arg Trp Asn Leu Ala Ala Ala Ser Asp Ile Leu
            260                 265                 270

Arg Ile Ser Ala Leu Lys Glu Ile Gly Gly Met Tyr Leu Asp Val Asn
            275                 280                 285

Met Leu Pro Gly Ile Gln Pro Asp Leu Phe Glu Ser Ile Glu Lys Pro
            290                 295                 300

Ser Ser Val Thr Val Asp Phe Trp Glu Met Thr Lys Leu Glu Ala Ile
305                 310                 315                 320

Met Lys Tyr Lys Glu Tyr Ile Pro Glu Tyr Thr Ser Glu His Phe Asp
                325                 330                 335

Met Leu Asp Glu Glu Val Gln Ser Ser Phe Glu Ser Val Leu Ala Ser
            340                 345                 350

Lys Ser Asp Lys Ser Glu Ile Phe Ser Ser Leu Gly Asp Met Glu Ala
            355                 360                 365

Ser Pro Leu Glu Val Lys Ile Ala Phe Asn Ser Lys Gly Ile Ile Asn
            370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Thr Asn Thr Phe Ile
            420                 425                 430

Asp Ser Ile Met Ala Glu Ala Asn Ala Asp Asn Gly Arg Phe Met Met
            435                 440                 445

Glu Leu Gly Lys Tyr Leu Arg Val Gly Phe Phe Pro Asp Val Lys Thr
            450                 455                 460

Thr Ile Asn Leu Ser Gly Pro Glu Ala Tyr Ala Ala Tyr Gln Asp
465                 470                 475                 480

Leu Leu Met Phe Lys Glu Gly Ser Met Asn Ile His Leu Ile Glu Ala
                485                 490                 495

Asp Leu Arg Asn Phe Glu Ile Ser Lys Thr Asn Ile Ser Gln Ser Thr
            500                 505                 510

Glu Gln Glu Met Ala Ser Leu Trp Ser Phe Asp Asp Ala Arg Ala Lys
            515                 520                 525

Ala Gln Phe Glu Glu Tyr Lys Arg Asn Tyr Phe Glu Gly Ser Leu Gly
            530                 535                 540

Glu Asp Asp Asn Leu Asp Phe Ser Gln Asn Ile Val Val Asp Lys Glu
545                 550                 555                 560

Tyr Leu Leu Glu Lys Ile Ser Ser Leu Ala Arg Ser Ser Glu Arg Gly
                565                 570                 575

Tyr Ile His Tyr Ile Val Gln Leu Gln Gly Asp Lys Ile Ser Tyr Glu
            580                 585                 590

Ala Ala Cys Asn Leu Phe Ala Lys Thr Pro Tyr Asp Ser Val Leu Phe
            595                 600                 605
```

-continued

```
Gln Lys Asn Ile Glu Asp Ser Glu Ile Ala Tyr Tyr Asn Pro Gly
    610                 615                 620
Asp Gly Glu Ile Gln Glu Ile Asp Lys Tyr Lys Ile Pro Ser Ile Ile
625                 630                 635                 640
Ser Asp Arg Pro Lys Ile Lys Leu Thr Phe Ile Gly His Gly Lys Asp
                645                 650                 655
Glu Phe Asn Thr Asp Ile Phe Ala Gly Phe Asp Val Asp Ser Leu Ser
                660                 665                 670
Thr Glu Ile Glu Ala Ala Ile Asp Leu Ala Lys Glu Asp Ile Ser Pro
            675                 680                 685
Lys Ser Ile Glu Ile Asn Leu Leu Gly Ala Asn Met Phe Ser Tyr Ser
    690                 695                 700
Ile Asn Val Glu Thr Tyr Pro Gly Lys Leu Leu Lys Val Lys
705                 710                 715                 720
Asp Lys Ile Ser Glu Leu Met Pro Ser Ile Ser Gln Asp Ser Ile Ile
                725                 730                 735
Val Ser Ala Asn Gln Tyr Glu Val Arg Ile Asn Ser Glu Gly Arg Arg
                740                 745                 750
Glu Leu Leu Asp His Ser Gly Glu Trp Ile Asn Lys Glu Glu Ser Gly
    755                 760                 765
Gly Ser Gly Lys Met Val Thr Gly Val Phe Lys Gly Pro Asn Gly Phe
770                 775                 780
Glu Tyr Phe Ala Pro Ala Asn Thr His Asn Asn Asn Ile Glu Gly Gln
785                 790                 795                 800
Ala Ile Val Tyr Gln Asn Lys Phe Leu Thr Leu Asn Gly Lys Lys Tyr
                805                 810                 815
Tyr Phe Asp Asn Asp Ser Lys Ala Val Thr Gly Trp Gln Thr Ile Asp
                820                 825                 830
Gly Lys Lys Tyr Tyr Phe Asn Leu Asn Thr Ala Glu Ala Ala Thr Gly
            835                 840                 845
Trp Gln Thr Ile Asp Gly Lys Lys Tyr Tyr Phe Asn Leu Asn Thr Ala
    850                 855                 860
Glu Ala Ala Thr Gly Trp Gln Thr Ile Asp Gly Lys Lys Tyr Tyr Phe
865                 870                 875                 880
Asn Thr Asn Thr Phe Ile Ala Ser Thr Gly Tyr Thr Ser Ile Asn Gly
                885                 890                 895
Lys His Phe Tyr Phe Asn Thr Asp Gly Ile Met Gln Ile Gly Val Phe
                900                 905                 910
Lys Gly Pro Asn Gly Phe Glu Tyr Phe Ala Pro Ala Asn Thr Asp Ala
            915                 920                 925
Asn Asn Ile Glu Gly Gln Ala Ile Leu Tyr Gln Asn Lys Phe Leu Thr
    930                 935                 940
Leu Asn Gly Lys Lys Tyr Tyr Phe Gly Ser Asp Ser Lys Ala Val Thr
945                 950                 955                 960
Gly Leu Arg Thr Ile Asp Gly Lys Lys Tyr Tyr Phe Asn Thr Asn Thr
                965                 970                 975
Ala Val Ala Val Thr Gly Trp Gln Thr Ile Asn Gly Lys Lys Tyr Tyr
                980                 985                 990
Phe Asn Thr Asn Thr Ser Ile Ala Ser Thr Gly Tyr Thr Ile Ile Ser
        995                 1000                1005
Gly Lys His Phe Tyr Phe Asn Thr Asp Gly Ile Met Gln Ile Gly
    1010                1015                1020
```

```
Val Phe Lys Gly Pro Asp Gly Phe Glu Tyr Phe Ala Pro Ala Asn
    1025                1030                1035

Thr Asp Ala Asn Asn Ile Glu Gly Gln Ala Ile Arg Tyr Gln Asn
    1040                1045                1050

Arg Phe Leu Tyr Leu His Asp Asn Ile Tyr Tyr Phe Gly Asn Asn
    1055                1060                1065

Ser Lys Ala Ala Thr Gly Trp Val Thr Ile Asp Gly Asn Arg Tyr
    1070                1075                1080

Tyr Phe Glu Pro Asn Thr Ala Met Gly Ala Asn Gly Tyr Lys Thr
    1085                1090                1095

Ile Asp Asn Lys Asn Phe Tyr Phe Arg Asn Gly Leu Pro Gln Ile
    1100                1105                1110

Gly Val Phe Lys Gly Ser Asn Gly Phe Glu Tyr Phe Ala Pro Ala
    1115                1120                1125

Asn Thr Asp Ala Asn Asn Ile Glu Gly Gln Ala Ile Arg Tyr Gln
    1130                1135                1140

Asn Arg Phe Leu His Leu Leu Gly Lys Ile Tyr Tyr Phe Gly Asn
    1145                1150                1155

Asn Ser Lys Ala Val Thr Gly Trp Gln Thr Ile Asn Gly Lys Val
    1160                1165                1170

Tyr Tyr Phe Met Pro Asp Thr Ala Met Ala Ala Ala Gly Gly Leu
    1175                1180                1185

Phe Glu Ile Asp Gly Val Ile Tyr Phe Phe Gly Val Asp Gly Val
    1190                1195                1200

Lys Ala Pro Gly Ile Tyr Gly Gly Ser Gly Ala Gln Val Ile
    1205                1210                1215

Asn Thr Asn Ser Leu Ser Leu Leu Thr Gln Asn Asn Leu Asn Lys
    1220                1225                1230

Ser Gln Ser Ala Leu Gly Thr Ala Ile Glu Arg Leu Ser Ser Gly
    1235                1240                1245

Leu Arg Ile Asn Ser Ala Lys Asp Asp Ala Ala Gly Gln Ala Ile
    1250                1255                1260

Ala Asn Arg Phe Thr Ala Asn Ile Lys Gly Leu Thr Gln Ala Ser
    1265                1270                1275

Arg Asn Ala Asn Asp Gly Ile Ser Ile Ala Gln Thr Thr Glu Gly
    1280                1285                1290

Ala Leu Asn Glu Ile Asn Asn Asn Leu Gln Arg Val Arg Glu Leu
    1295                1300                1305

Ala Val Gln Ser Ala Asn Ser Thr Asn Ser Gln Ser Asp Leu Asp
    1310                1315                1320

Ser Ile Gln Ala Glu Ile Thr Gln Arg Leu Asn Glu Ile Asp Arg
    1325                1330                1335

Val Ser Gly Gln Thr Gln Phe Asn Gly Val Lys Val Leu Ala Gln
    1340                1345                1350

Asp Asn Thr Leu Thr Ile Gln Val Gly Ala Asn Asp Gly Glu Thr
    1355                1360                1365

Ile Asp Ile Asp Leu Lys Gln Ile Asn Ser Gln Thr Leu Gly Leu
    1370                1375                1380

Asp Thr Leu Asn Val Gln Gln Lys Tyr Lys Val Ser Asp Thr Ala
    1385                1390                1395

Ala Thr Val Thr Gly Tyr Ala Asp Thr Thr Ile Ala Leu Asp Asn
    1400                1405                1410

Ser Thr Phe Lys Ala Ser Ala Thr Gly Leu Gly Gly Thr Asp Gln
```

Lys Ile Asp Gly Asp Leu Lys Phe Asp Asp Thr Gly Lys Tyr
1430                1435                1440

Tyr Ala Lys Val Thr Val Thr Gly Gly Thr Gly Lys Asp Gly Tyr
1445                1450                1455

Tyr Glu Val Ser Val Asp Lys Thr Asn Gly Glu Val Thr Leu Ala
1460                1465                1470

Gly Gly Ala Thr Ser Pro Leu Thr Gly Gly Leu Pro Ala Thr Ala
1475                1480                1485

Thr Glu Asp Val Lys Asn Val Gln Val Ala Asn Ala Asp Leu Thr
1490                1495                1500

Glu Ala Lys Ala Ala Leu Thr Ala Ala Gly Val Thr Gly Thr Ala
1505                1510                1515

Ser Val Val Lys Met Ser Tyr Thr Asp Asn Asn Gly Lys Thr Ile
1520                1525                1530

Asp Gly Gly Leu Ala Val Lys Val Gly Asp Asp Tyr Tyr Ser Ala
1535                1540                1545

Thr Gln Asn Lys Asp Gly Ser Ile Ser Ile Asn Thr Thr Lys Tyr
1550                1555                1560

Thr Ala Asp Asp Gly Thr Ser Lys Thr Ala Leu Asn Lys Leu Gly
1565                1570                1575

Gly Ala Asp Gly Lys Thr Glu Val Val Ser Ile Gly Gly Lys Thr
1580                1585                1590

Tyr Ala Ala Ser Lys Ala Glu Gly His Asn Phe Lys Ala Gln Pro
1595                1600                1605

Asp Leu Ala Glu Ala Ala Ala Thr Thr Thr Glu Asn Pro Leu Gln
1610                1615                1620

Lys Ile Asp Ala Ala Leu Ala Gln Val Asp Thr Leu Arg Ser Asp
1625                1630                1635

Leu Gly Ala Val Gln Asn Arg Phe Asn Ser Ala Ile Thr Asn Leu
1640                1645                1650

Gly Asn Thr Val Asn Asn Leu Thr Ser Ala Arg Ser Arg Ile Glu
1655                1660                1665

Asp Ser Asp Tyr Ala Thr Glu Val Ser Asn Met Ser Arg Ala Gln
1670                1675                1680

Ile Leu Gln Gln Ala Gly Thr Ser Val Leu Ala Gln Ala Asn Gln
1685                1690                1695

Val Pro Gln Asn Val Leu Ser Leu Leu Arg
1700                1705

<210> SEQ ID NO 8
<211> LENGTH: 767
<212> TYPE: PRT
<213> ORGANISM: Clostridium difficile

<400> SEQUENCE: 8

Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
                20                  25                  30

Glu Tyr His Asn Met Ser Glu Asn Thr Val Val Glu Lys Tyr Leu Lys
            35                  40                  45

Leu Lys Asp Ile Asn Ser Leu Thr Asp Ile Tyr Ile Asp Thr Tyr Lys
        50                  55                  60

```
Lys Ser Gly Arg Asn Lys Ala Leu Lys Lys Phe Lys Glu Tyr Leu Val
 65                  70                  75                  80

Thr Glu Val Leu Glu Leu Lys Asn Asn Leu Thr Pro Val Glu Lys
                 85                  90                  95

Asn Leu His Phe Val Cys Ile Gly Gly Gln Ile Asn Asp Thr Ala Ile
            100                 105                 110

Asn Tyr Ile Asn Gln Trp Lys Asp Val Asn Ser Asp Tyr Asn Val Asn
            115                 120                 125

Val Phe Tyr Asp Ser Asn Ala Phe Leu Ile Asn Thr Leu Lys Lys Thr
        130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
            180                 185                 190

Gln Arg Glu Glu Asn Pro Glu Leu Ile Ile Asp Asp Ile Val Lys Thr
            195                 200                 205

Tyr Leu Ser Asn Glu Tyr Ser Lys Glu Ile Asp Glu Leu Asn Thr Tyr
        210                 215                 220

Ile Glu Glu Ser Leu Asn Lys Ile Thr Gln Asn Ser Gly Asn Asp Val
225                 230                 235                 240

Arg Asn Phe Glu Glu Phe Lys Asn Gly Glu Ser Phe Asn Leu Tyr Glu
                245                 250                 255

Gln Glu Leu Val Glu Arg Trp Asn Leu Ala Ala Ala Ser Asp Ile Leu
            260                 265                 270

Arg Ile Ser Ala Leu Lys Glu Ile Gly Gly Met Tyr Leu Asp Val Asp
        275                 280                 285

Met Leu Pro Gly Ile Gln Pro Asp Leu Phe Glu Ser Ile Glu Lys Pro
        290                 295                 300

Ser Ser Val Thr Val Asp Phe Trp Glu Met Thr Lys Leu Glu Ala Ile
305                 310                 315                 320

Met Lys Tyr Lys Glu Tyr Ile Pro Glu Tyr Thr Ser Glu His Phe Asp
                325                 330                 335

Met Leu Asp Glu Glu Val Gln Ser Ser Phe Glu Ser Val Leu Ala Ser
            340                 345                 350

Lys Ser Asp Lys Ser Glu Ile Phe Ser Ser Leu Gly Asp Met Glu Ala
        355                 360                 365

Ser Pro Leu Glu Val Lys Ile Ala Phe Asn Ser Lys Gly Ile Ile Asn
        370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Thr Asn Thr Phe Ile
            420                 425                 430

Asp Ser Ile Met Ala Glu Ala Asn Ala Asp Asn Gly Arg Phe Met Met
        435                 440                 445

Glu Leu Gly Lys Tyr Leu Arg Val Gly Phe Phe Pro Asp Val Lys Thr
        450                 455                 460

Thr Ile Asn Leu Ser Gly Pro Glu Ala Tyr Ala Ala Ala Tyr Gln Asp
465                 470                 475                 480

Leu Leu Met Phe Lys Glu Gly Ser Met Asn Ile His Leu Ile Glu Ala
```

```
              485                 490                 495
Asp Leu Arg Asn Phe Glu Ile Ser Lys Thr Asn Ile Ser Gln Ser Thr
            500                 505                 510

Glu Gln Glu Met Ala Ser Leu Trp Ser Phe Asp Asp Ala Arg Ala Lys
            515                 520                 525

Ala Gln Phe Glu Glu Tyr Lys Arg Asn Tyr Phe Glu Gly Ser Leu Gly
            530                 535                 540

Glu Asp Asp Asn Leu Asp Phe Ser Gln Asn Ile Val Asp Lys Glu
545                 550                 555                 560

Tyr Leu Glu Lys Ile Ser Ser Leu Ala Arg Ser Ser Glu Arg Gly
            565                 570                 575

Tyr Ile His Tyr Ile Val Gln Leu Gln Gly Asp Lys Ile Ser Tyr Glu
            580                 585                 590

Ala Ala Cys Asn Leu Phe Ala Lys Thr Pro Tyr Asp Ser Val Leu Phe
            595                 600                 605

Gln Lys Asn Ile Glu Asp Ser Glu Ile Ala Tyr Tyr Asn Pro Gly
            610                 615                 620

Asp Gly Glu Ile Gln Glu Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
            645                 650                 655

Glu Phe Asn Thr Asp Ile Phe Ala Gly Phe Asp Val Asp Ser Leu Ser
            660                 665                 670

Thr Glu Ile Glu Ala Ala Ile Asp Leu Ala Lys Glu Asp Ile Ser Pro
            675                 680                 685

Lys Ser Ile Glu Ile Asn Leu Leu Gly Cys Asn Met Phe Ser Tyr Ser
            690                 695                 700

Ile Asn Val Glu Glu Thr Tyr Pro Gly Lys Leu Leu Leu Lys Val Lys
705                 710                 715                 720

Asp Lys Ile Ser Glu Leu Met Pro Ser Ile Ser Gln Asp Ser Ile Ile
            725                 730                 735

Val Ser Ala Asn Gln Tyr Glu Val Arg Ile Asn Ser Glu Gly Arg Arg
            740                 745                 750

Glu Leu Leu Asp His Ser Gly Glu Trp Ile Asn Lys Glu Glu Ser
            755                 760                 765

<210> SEQ ID NO 9
<211> LENGTH: 439
<212> TYPE: PRT
<213> ORGANISM: Clostridium difficile

<400> SEQUENCE: 9

Lys Met Val Thr Gly Val Phe Lys Gly Pro Asn Gly Phe Glu Tyr Phe
1               5                   10                  15

Ala Pro Ala Asn Thr His Asn Asn Ile Glu Gly Gln Ala Ile Val
            20                  25                  30

Tyr Gln Asn Lys Phe Leu Thr Leu Asn Gly Lys Lys Tyr Phe Asp
            35                  40                  45

Asn Asp Ser Lys Ala Val Thr Gly Trp Gln Thr Ile Asp Gly Lys Lys
            50                  55                  60

Tyr Tyr Phe Asn Leu Asn Thr Ala Glu Ala Ala Thr Gly Trp Gln Thr
65                  70                  75                  80

Ile Asp Gly Lys Lys Tyr Tyr Phe Asn Leu Asn Thr Ala Glu Ala Ala
            85                  90                  95
```

```
Thr Gly Trp Gln Thr Ile Asp Gly Lys Lys Tyr Tyr Phe Asn Thr Asn
                100                 105                 110
Thr Phe Ile Ala Ser Thr Gly Tyr Thr Ser Ile Asn Gly Lys His Phe
            115                 120                 125
Tyr Phe Asn Thr Asp Gly Ile Met Gln Ile Gly Val Phe Lys Gly Pro
        130                 135                 140
Asn Gly Phe Glu Tyr Phe Ala Pro Ala Asn Thr Asp Ala Asn Asn Ile
145                 150                 155                 160
Glu Gly Gln Ala Ile Leu Tyr Gln Asn Lys Phe Leu Thr Leu Asn Gly
                165                 170                 175
Lys Lys Tyr Tyr Phe Gly Ser Asp Ser Lys Ala Val Thr Gly Leu Arg
            180                 185                 190
Thr Ile Asp Gly Lys Lys Tyr Tyr Phe Asn Thr Asn Thr Ala Val Ala
        195                 200                 205
Val Thr Gly Trp Gln Thr Ile Asn Gly Lys Lys Tyr Tyr Phe Asn Thr
210                 215                 220
Asn Thr Ser Ile Ala Ser Thr Gly Tyr Thr Ile Ile Ser Gly Lys His
225                 230                 235                 240
Phe Tyr Phe Asn Thr Asp Gly Ile Met Gln Ile Gly Val Phe Lys Gly
                245                 250                 255
Pro Asp Gly Phe Glu Tyr Phe Ala Pro Ala Asn Thr Asp Ala Asn Asn
            260                 265                 270
Ile Glu Gly Gln Ala Ile Arg Tyr Gln Asn Arg Phe Leu Tyr Leu His
        275                 280                 285
Asp Asn Ile Tyr Tyr Phe Gly Asn Asn Ser Lys Ala Ala Thr Gly Trp
290                 295                 300
Val Thr Ile Asp Gly Asn Arg Tyr Tyr Phe Glu Pro Asn Thr Ala Met
305                 310                 315                 320
Gly Ala Asn Gly Tyr Lys Thr Ile Asp Asn Lys Asn Phe Tyr Phe Arg
                325                 330                 335
Asn Gly Leu Pro Gln Ile Gly Val Phe Lys Gly Ser Asn Gly Phe Glu
            340                 345                 350
Tyr Phe Ala Pro Ala Asn Thr Asp Ala Asn Asn Ile Glu Gly Gln Ala
        355                 360                 365
Ile Arg Tyr Gln Asn Arg Phe Leu His Leu Leu Gly Lys Ile Tyr Tyr
370                 375                 380
Phe Gly Asn Asn Ser Lys Ala Val Thr Gly Trp Gln Thr Ile Asn Gly
385                 390                 395                 400
Lys Val Tyr Tyr Phe Met Pro Asp Thr Ala Met Ala Ala Ala Gly Gly
                405                 410                 415
Leu Phe Glu Ile Asp Gly Val Ile Tyr Phe Phe Gly Val Asp Gly Val
            420                 425                 430
Lys Ala Pro Gly Ile Tyr Gly
        435

<210> SEQ ID NO 10
<211> LENGTH: 203
<212> TYPE: PRT
<213> ORGANISM: Clostridium difficile

<400> SEQUENCE: 10

Ile Thr Gly Phe Val Thr Val Gly Asp Asp Lys Tyr Tyr Phe Asn Pro
1               5                   10                  15
Ile Asn Gly Gly Ala Ala Ser Ile Gly Glu Thr Ile Ile Asp Asp Lys
            20                  25                  30
```

```
Asn Tyr Tyr Phe Asn Gln Ser Gly Val Leu Gln Thr Gly Val Phe Ser
             35                  40                  45

Thr Glu Asp Gly Phe Lys Tyr Phe Ala Pro Ala Asn Thr Leu Asp Glu
 50                  55                  60

Asn Leu Glu Gly Glu Ala Ile Asp Phe Thr Gly Lys Leu Ile Ile Asp
 65                  70                  75                  80

Glu Asn Ile Tyr Tyr Phe Asp Asp Asn Tyr Arg Gly Ala Val Glu Trp
                 85                  90                  95

Lys Glu Leu Asp Gly Glu Met His Tyr Phe Ser Pro Glu Thr Gly Lys
                100                 105                 110

Ala Phe Lys Gly Leu Asn Gln Ile Gly Asp Tyr Lys Tyr Tyr Phe Asn
                115                 120                 125

Ser Asp Gly Val Met Gln Lys Gly Phe Val Ser Ile Asn Asp Asn Lys
    130                 135                 140

His Tyr Phe Asp Asp Ser Gly Val Met Lys Val Gly Tyr Thr Glu Ile
145                 150                 155                 160

Asp Gly Lys His Phe Tyr Phe Ala Glu Asn Gly Glu Met Gln Ile Gly
                165                 170                 175

Val Phe Asn Thr Glu Asp Gly Phe Lys Tyr Phe Ala His His Asn Glu
                180                 185                 190

Asp Leu Gly Asn Glu Glu Gly Glu Glu Ile Ser
                195                 200

<210> SEQ ID NO 11
<211> LENGTH: 494
<212> TYPE: PRT
<213> ORGANISM: Clostridium difficile

<400> SEQUENCE: 11

Ala Gln Val Ile Asn Thr Asn Ser Leu Ser Leu Thr Gln Asn Asn
 1               5                  10                  15

Leu Asn Lys Ser Gln Ser Ala Leu Gly Thr Ala Ile Glu Arg Leu Ser
                 20                  25                  30

Ser Gly Leu Arg Ile Asn Ser Ala Lys Asp Asp Ala Ala Gly Gln Ala
             35                  40                  45

Ile Ala Asn Arg Phe Thr Ala Asn Ile Lys Gly Leu Thr Gln Ala Ser
 50                  55                  60

Arg Asn Ala Asn Asp Gly Ile Ser Ile Ala Gln Thr Thr Glu Gly Ala
 65                  70                  75                  80

Leu Asn Glu Ile Asn Asn Leu Gln Arg Val Arg Glu Leu Ala Val
                 85                  90                  95

Gln Ser Ala Asn Ser Thr Asn Ser Gln Ser Asp Leu Asp Ser Ile Gln
                100                 105                 110

Ala Glu Ile Thr Gln Arg Leu Asn Glu Ile Asp Arg Val Ser Gly Gln
                115                 120                 125

Thr Gln Phe Asn Gly Val Lys Val Leu Ala Gln Asp Asn Thr Leu Thr
    130                 135                 140

Ile Gln Val Gly Ala Asn Asp Gly Glu Thr Ile Asp Ile Asp Leu Lys
145                 150                 155                 160

Gln Ile Asn Ser Gln Thr Leu Gly Leu Asp Thr Leu Asn Val Gln Gln
                165                 170                 175

Lys Tyr Lys Val Ser Asp Thr Ala Ala Thr Val Thr Gly Tyr Ala Asp
                180                 185                 190

Thr Thr Ile Ala Leu Asp Asn Ser Thr Phe Lys Ala Ser Ala Thr Gly
```

```
                195                 200                 205
Leu Gly Gly Thr Asp Gln Lys Ile Asp Gly Asp Leu Lys Phe Asp Asp
        210                 215                 220

Thr Thr Gly Lys Tyr Tyr Ala Lys Val Thr Val Thr Gly Gly Thr Gly
225                 230                 235                 240

Lys Asp Gly Tyr Tyr Glu Val Ser Val Asp Lys Thr Asn Gly Glu Val
                245                 250                 255

Thr Leu Ala Gly Gly Ala Thr Ser Pro Leu Thr Gly Gly Leu Pro Ala
        260                 265                 270

Thr Ala Thr Glu Asp Val Lys Asn Val Gln Val Ala Asn Ala Asp Leu
        275                 280                 285

Thr Glu Ala Lys Ala Ala Leu Thr Ala Ala Gly Val Thr Gly Thr Ala
        290                 295                 300

Ser Val Val Lys Met Ser Tyr Thr Asp Asn Asn Gly Lys Thr Ile Asp
305                 310                 315                 320

Gly Gly Leu Ala Val Lys Val Gly Asp Asp Tyr Tyr Ser Ala Thr Gln
        325                 330                 335

Asn Lys Asp Gly Ser Ile Ser Ile Asn Thr Thr Lys Tyr Thr Ala Asp
        340                 345                 350

Asp Gly Thr Ser Lys Thr Ala Leu Asn Lys Leu Gly Gly Ala Asp Gly
        355                 360                 365

Lys Thr Glu Val Val Ser Ile Gly Gly Lys Thr Tyr Ala Ala Ser Lys
    370                 375                 380

Ala Glu Gly His Asn Phe Lys Ala Gln Pro Asp Leu Ala Glu Ala Ala
385                 390                 395                 400

Ala Thr Thr Thr Glu Asn Pro Leu Gln Lys Ile Asp Ala Ala Leu Ala
                405                 410                 415

Gln Val Asp Thr Leu Arg Ser Asp Leu Gly Ala Val Gln Asn Arg Phe
        420                 425                 430

Asn Ser Ala Ile Thr Asn Leu Gly Asn Thr Val Asn Asn Leu Thr Ser
        435                 440                 445

Ala Arg Ser Arg Ile Glu Asp Ser Asp Tyr Ala Thr Glu Val Ser Asn
    450                 455                 460

Met Ser Arg Ala Gln Ile Leu Gln Gln Ala Gly Thr Ser Val Leu Ala
465                 470                 475                 480

Gln Ala Asn Gln Val Pro Gln Asn Val Leu Ser Leu Leu Arg
                485                 490
```